(12) United States Patent
Gyrn et al.

(10) Patent No.: US 9,566,384 B2
(45) Date of Patent: Feb. 14, 2017

(54) INSERTION DEVICE WITH HORIZONTALLY MOVING PART

(75) Inventors: Steffen Gyrn, Ringsted (DK); Richard Morgan Hickmott, København Ø (DK); Alistair David Morton, Kastrup (DK); Henrik Jeppesen, Holte (DK)

(73) Assignee: UNOMEDICAL A/S, Birkeroed (DK)

( * ) Notice: Subject to any disclaimer, the term of this patent is extended or adjusted under 35 U.S.C. 154(b) by 1517 days.

(21) Appl. No.: 12/918,034

(22) PCT Filed: Feb. 19, 2009

(86) PCT No.: PCT/EP2009/051974
§ 371 (c)(1),
(2), (4) Date: Oct. 27, 2010

(87) PCT Pub. No.: WO2009/103759
PCT Pub. Date: Aug. 27, 2009

(65) Prior Publication Data
US 2011/0040254 A1 Feb. 17, 2011

Related U.S. Application Data

(60) Provisional application No. 61/030,022, filed on Feb. 20, 2008, provisional application No. 61/095,379, filed on Sep. 9, 2008.

(30) Foreign Application Priority Data

Feb. 21, 2008 (DK) .................................. 2008 00240

(51) Int. Cl.
*A61M 5/178* (2006.01)
*A61M 5/32* (2006.01)
(Continued)

(52) U.S. Cl.
CPC ......... *A61M 5/158* (2013.01); *A61M 5/14248* (2013.01); *A61M 5/1413* (2013.01);
(Continued)

(58) Field of Classification Search
CPC .............. A61M 5/158; A61M 5/14248; A61M 5/1412; A61M 2005/14252; A61M 2005/1585
(Continued)

(56) References Cited

U.S. PATENT DOCUMENTS 1,592,462 A    7/1926  MacGregor
2,047,010 A    7/1936  Dickinson
(Continued)

FOREIGN PATENT DOCUMENTS

DE    4 342 329 A1    6/1994
DE    196 31 921 A1   3/1997
(Continued)

OTHER PUBLICATIONS

International Search Report completed Jun. 17, 2009 for International Application No. PCT/EP2009/051974.
(Continued)

*Primary Examiner* — Matthew F Desanto
(74) *Attorney, Agent, or Firm* — Wilson Sonsini Goodrich & Rosati

(57) ABSTRACT

The invention relates to an insertion device comprising—a penetrating member (50) connected to transformation means (52), —a moving part (38) comprising guiding means (39) which guiding means (39) restrict the movement of the transformation means (52) and guide the penetrating member (50) from a first to a second position in a first direction, i.e. the direction of insertion, towards the injection site, and—a stationary housing (30) comprising guiding means (32) which guiding means (32) restrict the movement of the
(Continued)

moving part (38). The guiding means (32) guide the moving part (38) in a second direction which is linear and different from the first direction i.e. the direction of insertion.

18 Claims, 19 Drawing Sheets

(51) Int. Cl.
*A61M 5/158* (2006.01)
*A61M 5/142* (2006.01)
A61M 5/14 (2006.01)
A61M 39/26 (2006.01)

(52) U.S. Cl.
CPC .............. *A61M 2005/1426* (2013.01); *A61M 2005/14252* (2013.01); *A61M 2005/1585* (2013.01); *A61M 2005/1587* (2013.01); *A61M 2039/267* (2013.01)

(58) Field of Classification Search
USPC ............... 604/131–155, 175–179, 890.1
See application file for complete search history.

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A * | 12/1993 | Bachynsky .................. 604/134 |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |

(56) References Cited

U.S. PATENT DOCUMENTS

| | | |
|---|---|---|
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |

(56) References Cited

U.S. PATENT DOCUMENTS

| | | |
|---|---|---|
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 * | 12/2012 | Chong et al. ................. 604/180 |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |

(56) References Cited

U.S. PATENT DOCUMENTS

| | | |
|---|---|---|
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1* | 8/2004 | Hunn et al. ............... 604/164.01 |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0299409 A1 | 12/2007 | Whitbourne et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0775501 B1 | 5/1997 |
| EP | 0799626 A1 | 10/1997 |
| EP | 0937475 A2 | 8/1999 |

(56) References Cited

FOREIGN PATENT DOCUMENTS

| | | |
|---|---|---|
| EP | 0956879 A1 | 11/1999 |
| EP | 2272559 A1 | 1/2001 |
| EP | 1086718 A1 | 3/2001 |
| EP | 1125593 A1 | 8/2001 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A2 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A1 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2007140631 * | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/033702 A1 | 11/2008 |
| WO | WO 2008/135098 A1 | 11/2008 |
| WO | WO 2008/147600 A1 | 12/2008 |

(56) References Cited

FOREIGN PATENT DOCUMENTS

| WO | WO 2008/148714 A1 | 12/2008 |
|----|-------------------|---------|
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2012/041923 A2 | 9/2011 |
| WO | WO 2011/121023 A1 | 10/2011 |
| WO | WO 2012/041784 A1 | 4/2012 |
| WO | WO 2012/045667 A2 | 4/2012 |

OTHER PUBLICATIONS

International Preliminary Report on Patentability completed Jun. 29, 2010 for International Application No. PCT/EP2009/051974.
"Why inset®?" inset® infusion set product overview; http://web.archive.org/web/20040906102448/http://www.infusion-set.com/Default.asp?ID=108; two pages.

* cited by examiner

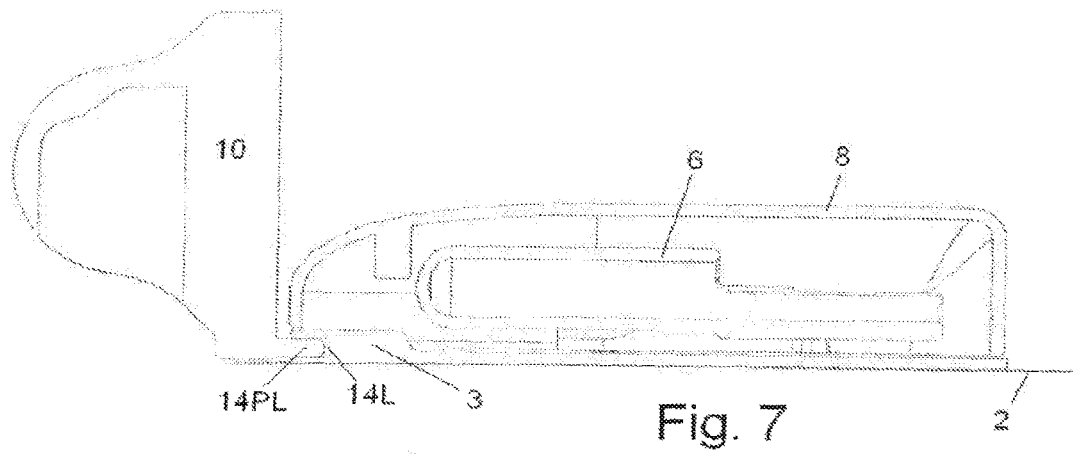
Fig. 7
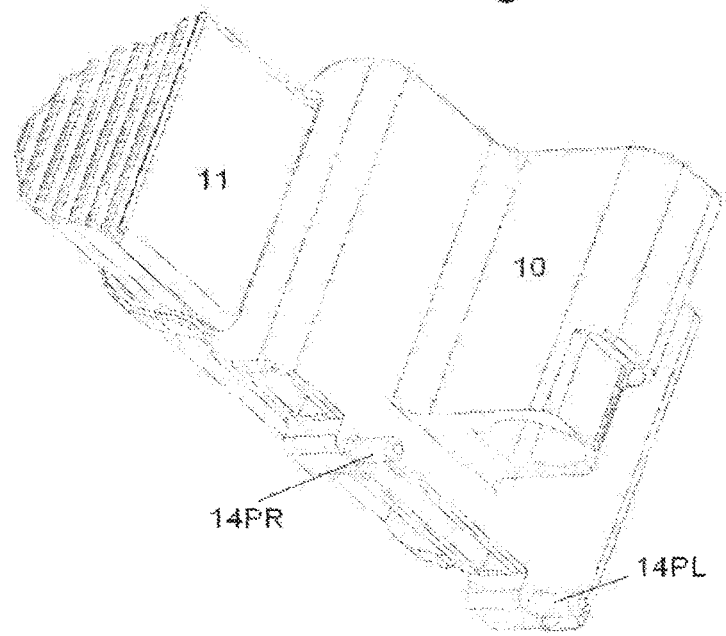

US 9,566,384 B2

INSERTION DEVICE WITH HORIZONTALLY MOVING PART

This application claims the benefit under 35 U.S.C. §371 of International Application No. PCT/EP2009/051974, filed Feb. 19, 2009, which claims the benefit of U.S. Provisional Application Ser. No. 61/030,022, filed Feb. 20, 2008, Danish Patent Application No. PA 2008 00240, filed Feb. 21, 2008, and U.S. Provisional Application Ser. No. 61/095,379, filed Sep. 9, 2008.

TECHNICAL FIELD OF THE INVENTION

The invention concerns an insertion device for inserting a medical device or a part of medical device into the subcutaneous or intramuscular area of a patient.

BACKGROUND OF THE INVENTION

An insertion device (also called inserter or injector) is commonly used in the medical field for inserting medical devices, such as infusion sets and the like, through the skin of a patient in a more or less automated fashion.

Commonly, when using an inserter, the user, i.e. the patient or the treatment provider (e.g. nurse, doctor, relative, or the like) has to apply a force towards the surface of the skin of the patient in order to provide injection of the medical device (needle, cannula, sensor, and the like). This can cause physiological or psychological distress and/or discomfort, and may lead to inappropriate application of the medical device. Many people are afraid of sharp objects, such as injection needles and other penetrating devices, commonly used for medical treatment and therapy. This fear is often irrational, and it may hamper an appropriate medical treatment. For example in the case of self-medication, a lack of administration of an appropriate dose of a required medical composition can lead to complications, which may even be life-threatening. When treating diabetes, e.g. in juveniles, there is a risk that the required insulin-dose may not be self-administered due to irrational fear of the insertion needle, combined with a general lack of knowledge and awareness concerning the consequences of omitting the correct application of the device and dosage.

A further known issue with insertion of medical devices is the risk of contamination of the penetrating member before or during application. This can easily lead to the introduction of an infection to a patient, e.g. through a contaminated insertion needle. The longer such a needle is exposed, the higher the risk of accidental contamination, e.g. by touching the needle with a finger, bringing the needle in contact with an unclean surface, or by airborne contamination, aerosol contamination and the like. Depending on the nature of the contamination (e.g. comprising virus, bacteria, fungus, yeast and/or prion) combined with the general health status of the patient, the resulting infection can rapidly turn into a life threatening situation.

Finally, it is well known that contact with an infected, used needle especially in hospital environments can be life-threatening, and the risk of accidental exposure to contaminated material in the form of a used insertion needle must be minimized.

The document WO 2002/002165 discloses a needle device having a needle retraction mechanism retracting the needle upon removing the device from a skin surface. The needle device comprises a penetrating member N connected to transformation means (44), an actuator (40) comprising guiding means restricting the movement of the transformation means and guiding the penetrating member N from a first to a second position in the direction of insertion towards the injection site. Further, the needle device comprises a stationary housing (20) provided with guiding means restricting the movement of the actuator (40). The actuator (40) and the attached needle N move in the same direction namely the direction of insertion. According to the present invention the penetrating part moves relative to the moving part and the moving part is fully separated from the penetrating part after insertion. This makes it possible to push the moving part in one direction with a simple spring mechanism while the penetrating member is guided to the injection site in the insertion direction. Separating the units and the direction optimises the possibility of individual control of each part when it comes to e.g. velocity and acceleration.

Thus, there is an obvious need in the art for a robust, reliable, accurate, safe, hygienic, and user friendly insertion device, which addresses the issues discussed above.

SUMMARY OF THE INVENTION

The current invention provides an insertion device for subcutaneously introduction of a penetrating member, where a "penetrating member" is understood to be a needle, a cannula, a sensor or the like. The penetrating member is normally prior and during insertion kept in a position where it is not visible to the patient and where it can not get in contact with the user or the patient before it is actually inserted.

The object of the invention is to provide an insertion device comprising
  a penetrating member connected to transformation means,
  a moving part comprising guiding means which guiding means restrict the movement of the transformation means and guide the penetrating member from a first to a second position in a first direction, i.e. the direction of insertion, towards the injection site, and
  a stationary housing comprising guiding means which guiding means restrict the movement of the moving part, which guiding means guide the moving part in a second direction which is linear and different from the first direction i.e. the direction of insertion.

According to one embodiment the second direction is perpendicular to the first direction but the second direction could be in any angle relative to the first direction, normally in an angle deviating 40-90° from the first direction.

"A stationary housing" means that the housing does not move relative to the insertion site during insertion. Often the contact between the guiding means restricting the movement of the transformation means and the transformation means are "sliding", this indicates that the contact between guiding means and the unit to be guided is continuous i.e. it is not interrupted but keep in contact with the guiding means at all positions.

According to one embodiment the insertion device comprises guiding means which restricts the movement of the penetrating member to a linear movement in the first direction. These guiding means assures that the penetrating member passes into the patients skin in a direction linear to the insertion direction during insertion, the time period defining "during insertion" is the time period which starts when the part of the penetrating member which is to be inserted into the skin of the patient is just about to penetrate the skin surface at the injection site and ends when the part of the penetrating member which is to be inserted is fully inserted. If the guiding means are not present the linear movement would be assured alone by regulation of the velocity of the penetrating member which is difficult especially when using simple and non-expensive components.

According to a further embodiment of the insertion device the first direction form an angle β to the surface in which the penetrating member is to be inserted, and where 30°≤β≤90°. The angle β is defined as the direction which the penetrating member moves in from the time just before the penetrating member touches the surface on which it is mounted and until the member is in its final position below the surface. This movement is linear. The penetrating member can be inserted at an inclined angle where β: 30°≤β<85° or 95°<β≤150°; normally an inclined angle will be around 45° i.e. 30°≤β<60° or 120°≤β<150°; or 40°≤β<50° or 130°≤β<140°; where said penetrating angle β is defined as the angle between the direction of penetrating movement of the penetrating member and surface on which it is mounted.

According to this embodiment of the insertion device the angle β can be essentially perpendicular to the surface on which it is mounted. That the penetrating direction is essentially perpendicular to the patients skin surface means that penetrating angle β=90°, normally a small deviation from 90° such as 85°≤β<95° would also be considered perpendicular to the skin surface.

According to a further embodiment of the insertion device the direction of the moving part during insertion is linear and essentially parallel to the surface on which it is mounted. That the direction is essentially parallel means that the angle between the direction of the moving part and the mounting surface at the insertion position is around 0°. There can be an inclination angle α: −45°<β<45°; wherein a positive inclination angle a indicates a movement inclined towards the skin surface, and a negative inclination angle indicates a movement inclined away from the skin surface. Normally there will be a deviation <10°, i.e. −10°<α<10°, between the surface of the patient's skin and the direction of the moving part. That the direction of the movement of the moving part is linear means that the moving part moves from a first point to a second point along a straight line.

According to a further embodiment of the insertion device a further movement of the moving part can provide a retraction movement of said holding means and/or an insertion needle. "A further movement" means that after a first movement i.e. the linear movement has ended at a second point, the forward movement of the moving part can continue to a third point where the forward movement of the moving part is stopped or alternatively the linear movement of the moving part can be reversed or take a second direction.

According to a further embodiment of the insertion device the insertion part can attached to a base part which base part can be fastened to the surface where the penetrating member is to be inserted and the penetrating member will be brought in contact with the base part upon insertion.

According to a further embodiment of the insertion device the penetrating member comprises a cannula, a body holding said cannula and retention means securing the body and the cannula at the surface of insertion. The cannula is held unreleasably by the body because the cannula is very small and difficult to handle by itself.

According to this embodiment of the insertion device the retention means can interact with interacting means on the base part upon insertion and retain the body of the penetrating member to the base part.

According to a further embodiment of the insertion device the guiding means of the moving part comprises a groove in which the transformation means of the penetrating member can slide. The groove can be essentially V- or U-shaped defining a starting point (22a), a middle point (22b) and an end point (22c) for the penetrating member (50) or at least parts of the penetrating member (50). Further the slope of the groove from the starting point to the middle point together with the velocity with which the moving part moves forward defines velocity of insertion. The slope of the groove is defined in relation to a coordinate system where the x-axis is placed horizontally i.e. along the surface on which the base part is placed and in the direction of the line formed by the moving part's forward movement (the moving part moves along the x-axis towards −∞), the y-axis is placed perpendicular to this surface. In such a coordinate system the groove will have a negative slop between the middle point and the starting point and the nominal size of the slope will influence the velocity of the penetrating member during insertion, the steeper the slope the faster the insertion. The slope or the tangent to the slope if the groove is curved i.e. not a straight line will normally be between −1 and −2. Further the slope of the groove from the middle point to the end point together with the velocity with which the moving part (38) moves forward defines velocity of retraction. The groove will have a positive slop between the middle point and the end point and the nominal size of the slope will influence the velocity of the penetrating member during retraction of a separate insertion needle or other parts of the penetrating member, the steeper the slope the faster the retraction. The slope or the tangent to the slope will normally be between 1 and 2.

According to a further embodiment of the insertion device the moving part can be moved as a consequence of either direct or indirect user input. That means that a user either provides a direct force to the device i.e. the user pushes or pulls the moving part or the user activates a spring or the like which then pushes or pulls the moving part.

According to this embodiment the insertion device moving of the moving part can be initiated by activating an activation part and the activation part is in contact with an energy storing member and influences the state of the energy storing member upon activation. Further the energy storing member can be a spring, and said spring is in a relaxed or partially relaxed state before activation and in a biased or distorted state after actuation of the activation part.

According to this embodiment of the insertion device the energy storing member provides the energy required for moving the moving part from a start position to a stop position.

According to one embodiment of the insertion device the housing can comprise retention means retaining the moving part in a start position, the moving part comprises locking means interacting with the retaining means in the start position and the activation part comprises interaction means interacting with the locking means upon activation. The locking means can be released from a locked position through interaction of the interaction means of the activation part. Further the locking means can have the form of a hook provided with an inclined surface pointing in the direction opposite to the forward movement of the activation part and the retention means can be a part protruding from the housing which can be caught by the hook formed by the locking means.

According to these embodiments the forward movement of the activation part is stopped through contact between the interaction means of the activation part and the retention means for the moving part.

According to one embodiment of the invention the groove is provided with a flexible part (39A) between the starting point (22*a*) and the middle point (22*b*) which flexible part (39A) can move in a direction opposite the direction of insertion. The flexible part (39A) can have the form of a protruding pivotable part (39A) having

- a contact surface which contact surface during movement is in contact with the transformation mean (51) of the cannula part (7) and pushes the cannula part (7) towards the injection site, and
- a non-contact surface opposite the contact surface which non-contact surface can move into an open room without getting into touch with other parts.

According to this embodiment the contact surface can have the form of two straight lines or flat surfaces connected in an angle n close to the point (D) (see FIG. 18*a*) where the cannula part (7) makes contact with the sealing of the surface plate (1), normally 10 degrees<n<45 degrees.

According to a further embodiment of the insertion device the moving part can be encompassed by the housing.

According to a further embodiment of the insertion device a base part can be fastened to the mounting surface and the insertion device can comprise means which means provide fastening of the insertion device to the base part before insertion and non-fastening of the insertion device to the base part upon insertion of the cannula.

According to this embodiment of the insertion device the means providing fastening and releasing of the insertion device from the base part comprise fastening means releasably locking the housing of the insertion device to the base part, and release means releasing the housing from the base part after insertion of the penetrating member. The release means can comprise an elastic member in a biased or distorted state which upon release of the fastening means pushes the housing of the insertion device away from the base part. The elastic member can have the form of a leaf spring which is positioned between the base part and the insertion device; the leaf spring will be distorted when the insertion device is locked to the base part.

According to these embodiments of the insertion device the fastening means which releasably lock the housing to the base part can have the form of a hook of a hard material being an integrated part of the housing catching a corresponding part of the base part. That the hook is an integrated part of the housing means that it forms part of the housing i.e. it is unreleasably locked to the housing and e.g. constructed as a part e.g. of a wall of the housing.

According to these embodiments of the insertion device the fastening means has the form of one or more protruding parts which protruding parts fit into corresponding openings in the base part. The one or more protruding parts can be removed from the corresponding openings in the base part by a rotating movement and the insertion device is mounted to the base part in such a distance from the surface in which the penetrating member is inserted that the distance allows for a rotating movement of the insertion device. The distance from the surface in which the penetrating member is inserted is obtained by constructing the insertion device with an inclining proximal surface which proximal surface as a result of the rotating movement gets parallel with the surface in which the penetrating member has been inserted.

According to these embodiments of the insertion device the fastening means can be flexibly connected to the stationary housing. The moving part can be provided with one or more protruding parts which upon movement of the moving part get in contact with the flexibly connected fastening means and through this contact release the insertion device from the base part.

According to a further embodiment of the insertion device the insertion device comprises means to perform the following operations upon actuation of an activation part:

(a) loading of a spring;
(b) movement of the moving part from a start position to a stop position; and
(c) transformation of said movement of the moving part to an insertion movement of a penetrating member, followed by a retraction movement of a holding means of the penetrating member.

This embodiment can further comprise means which can:

(d) release the housing from the base plate upon insertion of the penetrating member.

According to these embodiments of the insertion device the housing can be connected to the base plate via connection means. The connection means can comprise at least one hinge and at least one locking member.

According to these embodiments of the insertion device the housing can be released from the base plate by interaction of a releasing member with a part of a sidewall of the housing. Said part of a sidewall of the housing can be flexible, and can be twisted (pivoted) in relation to the remaining housing.

According to a further embodiment of the insertion device the penetrating member has a first position (i), and a second position (ii) relative to the stationary housing, where the penetrating member in the first position (i) is fully retracted and does not protrude from the housing of the insertion device; and in the second position (ii), a part of the penetrating member such as the cannula and/or insertion needle protrude maximally from the housing (30). The first retracted position is the position of the penetrating member before insertion and the second maximally protruding position is the position of the penetrating member just as the penetrating member has been fully inserted. The penetrating member can have a further third position (iii), where the cannula protrudes maximally from the housing, and the holding means and/or insertion needle are retracted into the housing and are no longer in contact with the body holding the cannula.

According to these embodiments of the insertion device the body of the penetrating member in the second position (ii) and in the third position (iii), is retained through interaction of said retention means of the body with interacting means on a base part.

According to a further embodiment of the insertion device the moving part can have a first position (i*), a second position (ii*), and optionally a third position (iii*) in relation to the housing and in the first position (i*) and the optionally third position (i*) the guiding means via the transformation means hold the holding means in a position retracted from the patients skin and in the second position (ii*) the guiding means hold the holding means in a position close to or in contact with the patient.

According to this embodiment of the insertion device the moving part is held in the first position (i*) by retention means unreleasably fastened to the housing, locking means unreleasably fastened to the moving part and interaction means unreleasably fastened to the activation part.

According to a further embodiment of the insertion device the kit further comprises a base part to which base part the insertion device is fastened at least before insertion and a delivery part which can be fastened to the base part and form a fluid path to a penetrating member inserted by the insertion device.

Definitions

"Parallel" or "essentially parallel" as used herein refers to a second movement in a direction, plane, item or the like defined in relation to a first or a reference plane or direction which reference plane or direction has a direction defined as the angle $\alpha=0°$; and the second plane or direction deviates at maximum $\pm 10°$; normally not more than $\pm 5°$ from the first or reference direction $\alpha$.

In the context of the application "horizontal" or "essentially horizontal" means that a movement in a direction, a direction, plane, item or the like is horizontal or essentially horizontal is parallel or essentially parallel to the surface of the skin of a patient as defined above. For example, the base part to which the insertion device is fastened can be horizontal, or essentially horizontal, parallel or essentially parallel to the skin.

"Perpendicular" or "essentially perpendicular" as used herein refers to a second movement in a direction, a direction, plane, item or the like defined in relation to a reference plane or direction which reference plane or direction has a position or a direction in the angle $\beta=0°$; and the second plane or direction deviates between 80-100°; normally between 85-95° from the first reference $\beta$.

In the context of the application "Transversal" or "essentially transversal" can be used interchangeably with perpendicular or essentially perpendicular as defined above.

"Means": As used herein, the expression means can comprise one or more means. This is irrespective, if with respect to grammar, the verb relating to said means indicates singular or plural.

BRIEF DESCRIPTION OF THE DRAWINGS

A detailed description of embodiments of the current invention will be made with reference to the accompanying figures, wherein like numerals designate corresponding parts in different figures.

FIG. 7 shows a longitudinal cut through an assembly as shown in FIG. 3-6, the cut is placed at the position of one of the fastening means for the insertion device.

FIG. 8 shows the insertion device without being attached to the base part.

FIG. 18b shows how the moving part 38 is viewed in FIG. 18a.

DETAILED DESCRIPTION OF THE INVENTION

Figure 1:
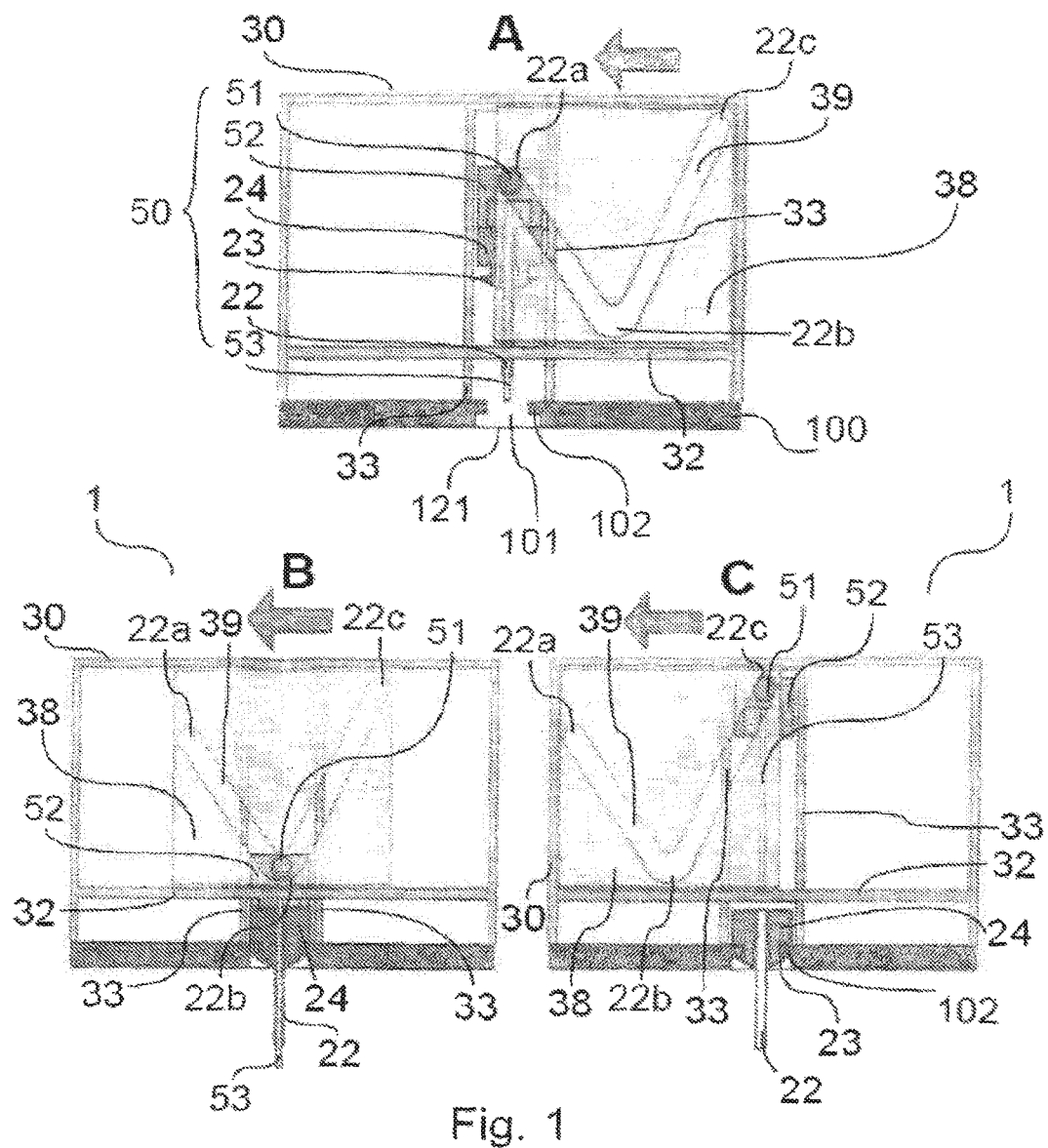
FIGS. 1A-C show a cross section of a first embodiment of an insertion device according to the invention in three states: A: before activation; B: just after insertion; C: after retraction of insertion needle.

FIGS. 1A-1C shows one embodiment of an insertion device 1 for inserting a penetrating member 50 according to the present invention.

The insertion device 1 comprises a housing 30, a base part 100, a moving part 38 and a penetrating member 50. For clarity, the moving part 38 is represented in a semi-transparent fashion. The FIGS. 1A, 1B and 1C show the penetrating member 50 in three different positions relative to the moving part 38.

The penetrating member 50 comprises holding means 52 holding the penetrating member 50, transformation means 51 attached to the holding means 52 of the penetrating member 50, a body 24, a cannula 22, and an insertion needle 53. The cannula 22 is according to this embodiment a soft cannula which needs to be inserted with the help of an insertion needle 53 which is attached unreleasably to a part of the insertion device and not to the penetrating member 50. The cannula 22 is attached unreleasably to the body 24. Furthermore, the body 24 comprises retention means 23 for fastening of the cannula 22 to the base part 100 when the cannula 22 has been fully inserted. According to this embodiment the retention means 23 are formed as mechanical hooks which can be forced inward i.e. toward the centre where the cannula 22 is positioned. As the mechanical hooks are fastened to the body 24 in a flexible way the hooks will return to their original position after having been forced towards the centre, the flexibility will normally be due to the properties of the material used to produce the body, the hooks and the connection formed between them.

In another embodiment of the invention, the penetrating member 50 comprises a sensor or both a sensor and a cannula. In a further embodiment of the invention, the penetrating member 50 comprises more than one cannula 22 e.g. a plurality of cannula and/or a plurality of sensors.

The housing 30 comprises guiding means 32 for the moving part 38 and guiding means 33 for the penetrating member 50. The guiding means 32 for the moving part 38 according to this embodiment comprises surfaces of the inner walls of the housing 30 along which the moving part 38 can slide and the guiding means 33 for the penetrating member 50 comprises an upright tube-like shape. The moving part 38 is provided with transformation means in the form of a V-shaped opening which is form to fit closely with the transformation means 51 of the penetrating member 50. The housing 30 is releasably connected to the base part 100, and can be disconnected from the base part 100 after the penetrating member 50 has been inserted. When connected, the housing 30 and the base part 100 encloses the penetrating member 50, the moving part 38, and the guiding means 32, 33 for the moving part 38 and the penetrating member 50, respectively thereby providing a unit.

The base part 100 comprises an opening 101, which is dimensioned to allow passage or entering of the penetrating member 50 or at least a part of it, such as the cannula 22, the injection needle 53 and the retention means 23.

The base part 100 and the housing 30 are normally individual elements, which elements can be separated in a reversible or an irreversible fashion. According to the present embodiment the opening 101 comprises interaction means 102, adapted to interact with the retention means 23 of the body of the penetrating member 50. The opening 101 can be closed and/or protected by a seal 121 which seal 121 is either removable or can be penetrated by the penetrating member 50. The seal 121 can cover a large area of the base part 100 and if the base part 100 is partly constituted by a mounting pad with an adhesive surface the seal 121 can be a release layer protecting the adhesive surface before use.

The guiding means 32 for the moving part 38 provides a directional controlled movement of the moving part 38 essentially within the housing 30. In the depicted embodiment the moving part 38 can move essentially parallel, i.e. essentially horizontal relative to the base part 100, guided by the guiding means 32. Such a movement can be characterised as a sliding movement.

The movement performed by the moving part 38 is a longitudinal movement, i.e. a linear movement relative to the housing 30. The means used to initiate and maintain the movement of the moving part 38 can either be provided directly by the user i.e. the user pushes or pulls the moving part 38 or it can be provided by mechanical means such as a spring which only has to be activated by the user The guiding means 33 for the penetrating member 50 which are a part of or connected to the moving part 38 provide a movement of the penetrating member 50 in a direction different from the direction of movement of the moving part 38. This feature has at least two advantages: 1. the user's actions when activating or pushing the moving part 38 is less likely to influence the actual insertion of the penetrating member 50, and 2. the insertion device can be constructed in a smaller and more compact manner.

According to the embodiment of FIG. 1 the direction of movement of the penetrating member 50 is essentially perpendicularly to the direction of movement of the moving part 38. The guiding means 33 for the penetrating member can comprise one or more parts which together provides a well defined track or tube along or in which the penetrating member can slide e.g. the guiding means 33 may comprise a hollow, cylindrical element fastened to the housing 30, the penetrating member 50 can move inside the cylindrical element along the longitudinal axis of said cylindrical element, comparable to the movement of a piston in a cylinder. Such a movement can be described as a sliding movement as the contact between the inner surfaces of the cylindrical element and the outer surfaces of the penetrating member 50 provides the guiding. Alternatively, the guiding means 33 of the penetrating member 50 can comprise one or more bars, governing the direction of movement of the penetrating member 50. As seen in FIG. 1, the guiding means 33 for the penetrating member 50 according to this embodiment extend from the inner ceiling of the housing to the base part 100. The guiding means 33 of the penetrating member 50 is not necessarily attached to the base part 100. The guiding means 33 normally e.g. rest against and/or touch and/or are connected with the base part 100. In the depicted embodiment, the guiding means 33 of the penetrating member 50 is connected to the housing 30 at the inside of the upper surface ("ceiling"), and at one or more side ("wall") of the housing 30.

The guiding means 39 or the transformation means of the moving part 38 for the transformation means 51 of the penetrating member 50 defines a track. This track extends from a starting point 22a to a middle point 22b and ends at an end point 22c. As seen in FIG. 1, this track is V-shaped, or essentially V-shaped. In the depicted embodiment, the guiding means 39 of the moving part 38 are provided as a continuous grove or through going opening within the moving part 38. The middle point 22b is closer to the base part 100 than the starting point 22a, and also closer to the base part 100 than the end point 22c, also, the starting point 22a is closer to the base part 100 than the end point 22c.

It is not essential how the starting point 22a and the end point 22c varies relative to each other, i.e. it would be possible to have an embodiment where the end point 22c is closer to base part 100 than start point 22a or an embodiment where the starting point 22a and the end point 22c have the same distance to the base part 100. It should though be assured that the starting point 22a is placed in a distance from the base part which is far enough to keep the end of the cannula 22 and the end of a separate insertion needle 53 inside the housing 30 before insertion.

According to the invention and as illustrated in FIG. 1A-1C, the insertion device 1 is adapted to provide:
(i) a first state (FIG. 1A), where the penetrating member 50 is in the starting position 22a, it is fully retracted and does not protrude from the housing 30 of the insertion device 1, the moving part 38 is in a start position in the right side of the housing 30;
(ii) a second state (FIG. 1B), where the penetrating member 50 is in the middle point 22b, the part(s) of the penetrating member 50 which are to be inserted, such as the cannula 22 and/or an insertion needle 53, fully protrude the housing 30 through the opening 101 in the base part 100, and the moving part 38 has been moved forward to a middle position relative to the housing 30. The stationary guiding means 33 of the penetrating member 50 prevent the penetrating member 50 from moving in the same direction as the moving part 38 and only allows a "vertical" movement of the penetrating member 50 i.e. vertical is here to be understood as being perpendicular to "horizontal"; and
(iii) a third position (FIG. 1C), where the part(s) of the penetrating member 50 to be inserted still protrude the housing 30, but the transformation means 51 together with the holding means 52 and the insertion needle 53 are at the end point 22c and the insertion needle has been retracted from the injection site. The moving part 38 has reached the end of its travel to the left in the stationary housing. In the second position (ii) and in the third position (iii), the body 24 of the penetrating member 50 is retained through interaction between the retention means 23 of the body 24 of the penetrating member 50 and the interacting means 102 of the base part 100.

As shown, the horizontally forward movement of the moving part 38 is transformed into an insertion movement of the penetrating member 50 followed by a retraction movement of one or more parts of the penetrating member 50. This is achieved by the interaction of the guiding means 39 of the moving part 38 with the transformation means 51 of the penetrating member 50.

In the first position (i), the transformation means 51 of the penetrating member 50 are at the starting point 22a of the track/guiding means 39. When the moving part 38 is moved horizontally guided by its guiding means 32, the penetrating member 50 is moved downwards, i.e. "vertically" towards the base part 100. The speed of the movement of the moving part 38 and the slope of the guiding means 39 define the speed of the movement of the penetrating member 50, thus the speed of insertion i.e. the steeper the slope of the guiding means 39 are, the shorter time will be used to guide the penetrating member 50 from the retracted start position to the inserted position.

In the second position (ii), the transformation means 51 of the penetrating member 50 have reached the middle point 22b of the guiding means 39. At this point the direction of the slope of the guiding means 39 changes from downwards, i.e. towards the base part 100, to upwards, i.e. away from the base part 100. Thus the orientation of the slope of the guiding means 39 defines the direction of movement of the penetrating member 50. Further the forward horizontal movement of the moving part 38 produces a retraction movement of the holding means 52 of the penetrating member 50 and the insertion needle 53. If the cannula 22 is a hard self penetrating cannula there will be no need of a separate insertion needle 53 and also there will be no need to perform the last retraction part of the movement i.e. the last line of the V in the track 39 could be left out and the middle point 22b would be identical to the end point 22c.

In the third position (iii), the transformation means 51 of the penetrating member 50 have reached the end point 22c of the guiding means 39, and the holding means 52 of penetrating member 50 and the insertion needle 53 are fully retracted.

As seen in FIG. 1, the moving part 38 does not protrude the housing 30. The arrow above the figure indicates the direction of movement of the moving part 38.

FIG. 2A-2F illustrates attachments means with an automatic release function. The insertion device 1 comprises a housing 30, a base part 100, a moving part 38, an activation part 11, and a penetrating member 50. One embodiment of a penetrating member 50 is shown in these figures but a penetrating member 50 similar to the penetrating members described in FIG. 16-17 might also be used. For illustrative purposes means the moving part 38 are represented in a semi-transparent fashion.

The housing 30 comprises guiding means 32 for the moving part 38 which allows the moving part 38 to move between at least two positions, guiding means 33 for the penetrating member 50 which allows the penetrating member 50 to move between at least two positions, and guiding means 34 for the activation part 11 which allows the activation part to move between at least two positions. The housing 30 is attached to the base part 100. According to this embodiment the attachment is releasable. The attachment is provided by parts of the housing 30 comprising a hinge 35 and fastening means 14 interacting with parts of the base part 100, whereby the housing 30 and the base part 100 are releasably connected. The hinge 35 comprises an at least partly rounded surface of a wall of the housing 30 which can pivot in relation to the base part 100 as it is placed in a groove in the base part 100. The fastening means 14 of the housing 30 interacts with locking means 108 of the base part 100.

The letter "b" in FIG. 2C indicates the height of the housing 30 of the insertion device 1. The height "b" will expediently be in the range of 5-100 mm, and normally in the range 10-50 mm or more specifically 20-30 mm. The illustrated embodiment is 25 mm. In embodiments where the inserter is not removed after inserted the inserter should be as low as possible and normally not extend further from the patients skin than the delivery part 8.

The housing 30 also comprises retention means 31. The retention means 31 hold the moving part 38 in a start position by engaging with locking means 28 on the moving part 38. According to this embodiment the retention means further provides a stop for the movement of the activation part 11.

The guiding means 32 for the moving part 38 provides a directional controlled movement of the moving part 38 in relation to the housing 30. The guiding means 32 are attached to or connected to or an integrated part of the inner surfaces of the housing 30 and will normally have the shape of longitudinal tracks corresponding to surfaces on the moving part 38 in order to make it possible for the moving part 38 to slide along the tracks. In the depicted embodiment, the moving part 38 can move parallel, i.e. horizontal to the base part 100, guided by the guiding means 32, the movement will normally be a sliding movement in a direction parallel to the surface of the base part 100, i.e. the movement is a longitudinal movement or a linear movement.

The guiding means 33 for the penetrating member 50 which are a part of or connected to or integrated with the housing 30 provides that the penetrating member 50 can only be moved in a well defined direction which direction is different from the direction of the moving member 38. In the embodiment the direction of movement of the penetrating member 50 is essentially perpendicularly to the direction of movement of the moving part 38. The guiding means 33 for the penetrating member 50 will normally be formed by inner surfaces of the housing 30, e.g. the guiding means 33 may comprise the inner surfaces of a hollow, cylindrical element wherein the penetrating member 50 can move between at least a forward and a retracted position along the longitudinal axis of said cylindrical element, comparable to the movement of a piston in a cylinder. If the penetrating member 50 has a rectangular cross-section the "cylindrical" element should of course be adapted to fit closely to the cross-section of the actually used penetrating member 50. Such a movement will be a sliding movement as the continuous contact between the inner surfaces of the cylindrical elements and the outer surfaces of the penetrating member 50 provides the guiding. Alternatively, the guiding means 33 of the penetrating member 50 can comprise one or more bars, governing the direction of movement of the penetrating member 50. As seen from the figures the guiding means 33 for the penetrating member 50 according to this embodiment can extend from the inner ceiling of the housing to the bottom part 100. The guiding means 33 of the penetrating member 50 are not attached to the base part 100 but might reach down and touch it or e.g. provide a support for the base part 100.

The guiding means 34 of the activation part 11 provides a directional controlled movement of the activation part 11 in relation to the housing 30. The guiding means 34 are attached to or integrated with the housing 30. In the depicted embodiment, the activation part 11 moves in parallel with, i.e. horizontal to the base part 100, guided by the guiding means 34 which according to this embodiment is provided as parts of the inner surfaces of the housing. The guiding means 34 might be formed as longitudinal tracks leading the activation part 11 in a well defined direction or simply the inner surfaces of the walls of the housing 30. Such a movement is normally a sliding movement as the guiding means 34 and the activation means are in continuous contact while moving in relation to each other. The movement will normally be a linear movement. The direction of movement of the activation part 11 is according to this embodiment identical to the direction of movement of the moving part 38 therefore the guiding means 34 of the activation part 11 can be the same as the guiding means 32 of the moving part 38 i.e. on set of guiding means 32, 34 provides the well defined and at least partly simultaneous movement of the moving part 38 and the activation part 11.

The moving part 38 is provided with transformation means 39 providing transformation of the movement of the moving part 38, which according to this embodiment is horizontal, into a movement of the penetrating member 50 in the insertion direction followed by a movement of at least the insertion needle of the penetrating member 50 in a direction of retraction. According to this embodiment the transformation means are in the form of a protruding cylindrical part 51 on the penetrating member 50 corresponding to an open V-shaped track 39 in the moving part 38. The V-shaped track 39 is sized to fit closely with the protruding part 51 of the penetrating member 50 in order to provide a well defined path of movement.

The moving part 38 comprises a releasing member 29 providing a separation of the housing 30, or at least a part of the housing 30, from the base part 100 by releasing the fastening means 14 of the housing from the locking means 108 of the base part 100. Said release is provided by interaction of the releasing member 29 with a part of the housing 30, according to this embodiment it is the inner wall of the housing 30 opposite the activation means 11 where the linear movement of the activation means 11 would end if continued to the inner wall of the housing 30.

The housing comprises an elastic member 36 which upon release of the fastening means 14 of the housing initiates removal of the housing 30 from the base part 100. According to the embodiment shown in FIG. 2 the elastic member 36 is an integrated part of the housing 30 i.e. it is fastened unreleasably to the housing 30. The elastic member 36 is a leaf spring unreleasably fastened to the housing 30 at one end and pressed against the base part 100 at the opposite end. The flexibility of the elastic member 36 is defined by the material of which it is constructed and the physical dimensions of the material, according to the present embodiment the elastic member is constructed of the same material as the housing i.e. a hard plastic and normally formed during molding of the housing 30, but it could also be constructed of a metal which after molding of the housing is fastened unreleasably to the housing 30.

Insertion of the penetrating member 50 using the insertion device according to the invention 1 is initiated by activation of the activation part 11. The activation part 11 is activated by pushing the part towards the housing 30. The activation part 11 comprises interaction means 41. The interaction means 41 interacts with the retention means 31 of the housing 30, thereby arresting the forward movement of the activation part 11. As can be seen in FIG. 2A, the activation part 11 protrudes the housing 30 in the depicted, non-activated state. The letter "a" indicates the length of protrusion of the activation part 11 with respect to the housing 30. The protrusion before activation of the activation part 11 will normally be in the range of 1-100 mm, or 5-50 mm, or 10-25 mm, or 15-20 mm. In the shown embodiment the protrusion is 17 mm. In another embodiment of the invention, the activation part 11 does not protrude the housing 30, or protrudes the housing 30 only marginally.

The insertion device 1 is in a non-activated state before use, such as during transport or storage.

According to this embodiment a spring 45 is provided between the moving part 38 and the activation part 11. Normally the spring 45 will be in a relaxed state during storing as this will normally prolong the time the product can be stored while still being fully functional, if the spring 45 is in a biased state during storing there is a risk that the performance of the product will rapidly decrease. As illustrated in FIG. 2A-F the spring 45 can be a spiral spring, comprising two ends: a first end 46, attached to, or placed in connection with the moving part 38 and a second end 47 attached to, or placed in connection with the activation part 11. The spring 45 is positioned along the direction of movement for the activation part 11 which is being parallel to the upper surface of the base part 100.

A function of the spring 45 is to provide energy for the penetration and/or retraction movement of the penetrating member 50 and/or parts of the penetrating member 50. If this energy is not provided by a spring 45 it has to be directly provided by the user of the device as the user provides a horizontal movement of the activation part 11 by pushing the activation part 11 towards the housing 30 and thereby a horizontal movement of the moving part 38.

The spring 45 of the illustrated embodiment stores energy from the movement of the actuation of the of the activation part 11 as the spring 45 is biased through this first movement. During actuation of the activation part 11 the moving part 38 is stationary. When the interaction means 41 of the activation part 11 gets into contact with the locking means 28, the moving part 38 is released from the stationary position and moved in a direction defined by the guiding means 32. The forward movement of the activation part 11 is stopped at the time where the interaction means 41 touches the retention means 31 of the housing 30. According to the embodiment of FIG. 2 the direction of the moving part 38 is the same as the forward direction of the activation part 11. When the moving part 38 pushed by the spring 45 hits the inner surface of the housing 30, the spring 45 is biased enough to provide energy for the release of the releasable connection between the fastening means 14 of the housing 30 and the locking means 108 of the base part 100. This is provided by making the wall or at least a part of the wall of the housing 30 so flexible that the wall can be bend outward and release the fastening means 14 from the locking means 108 of the base part 100. When the locking connection is released the elastic member 36 pushes the housing 30 away from the base part 100 and the user will not need pull the insertion device away from the base part 100.

Figure 3:
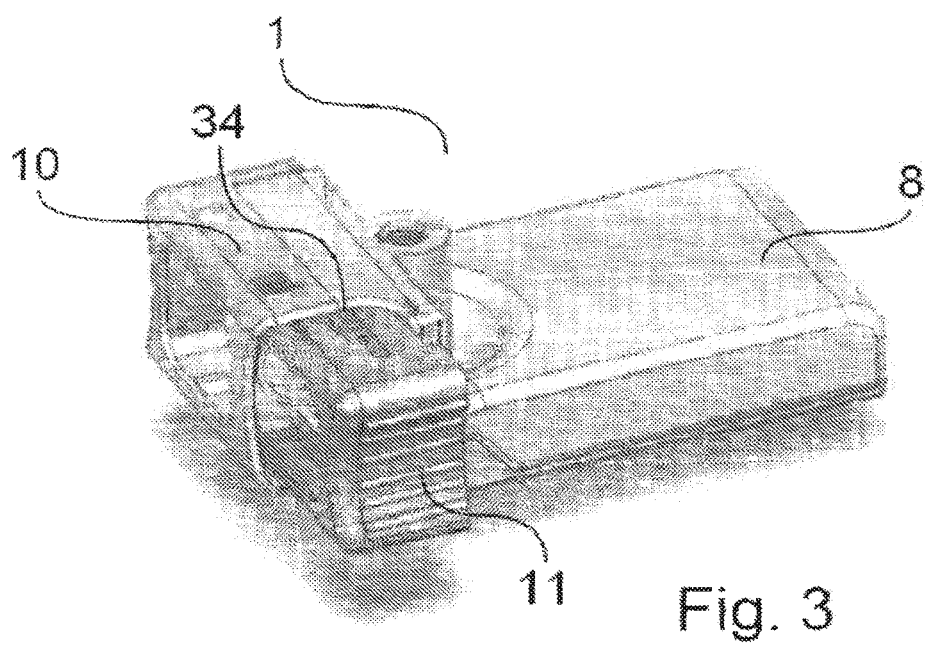
FIG. 3 shows a first embodiment of an assembly comprising an insertion device according to the invention.

FIG. 3 shows a first embodiment of an assembly comprising an inserter according to the invention together with a medication unit 8. Only the side of the base part 100 can be seen as the whole of the upper surface of the base part 100 is covered by the medication unit 8. The medication unit 8 will normally comprise both a reservoir for medication such as insulin and delivering parts in the form of pumping means and e.g. dosing means which can see to that the patient has a prescribed dose of medication.

Figure 4:
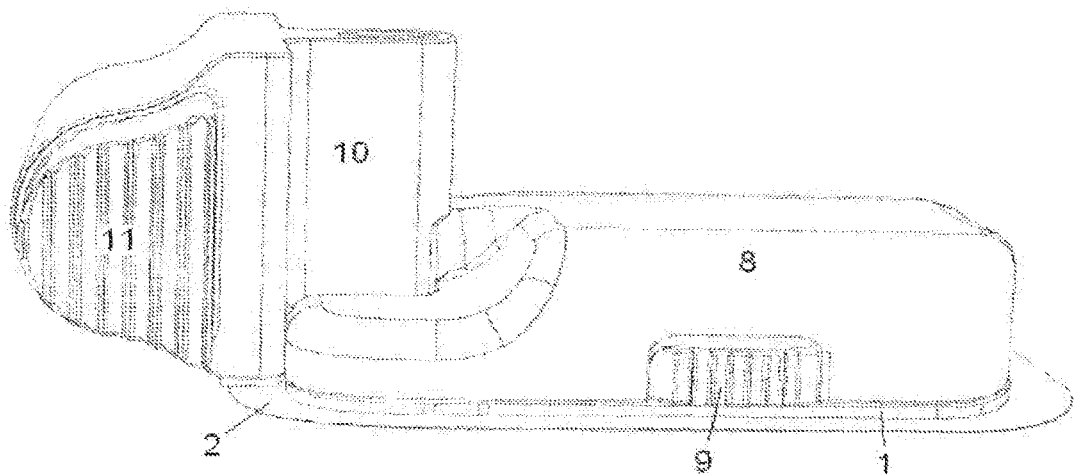
FIG. 4 shows a second embodiment of an assembly comprising an insertion device according to the invention.
Figure 5A:
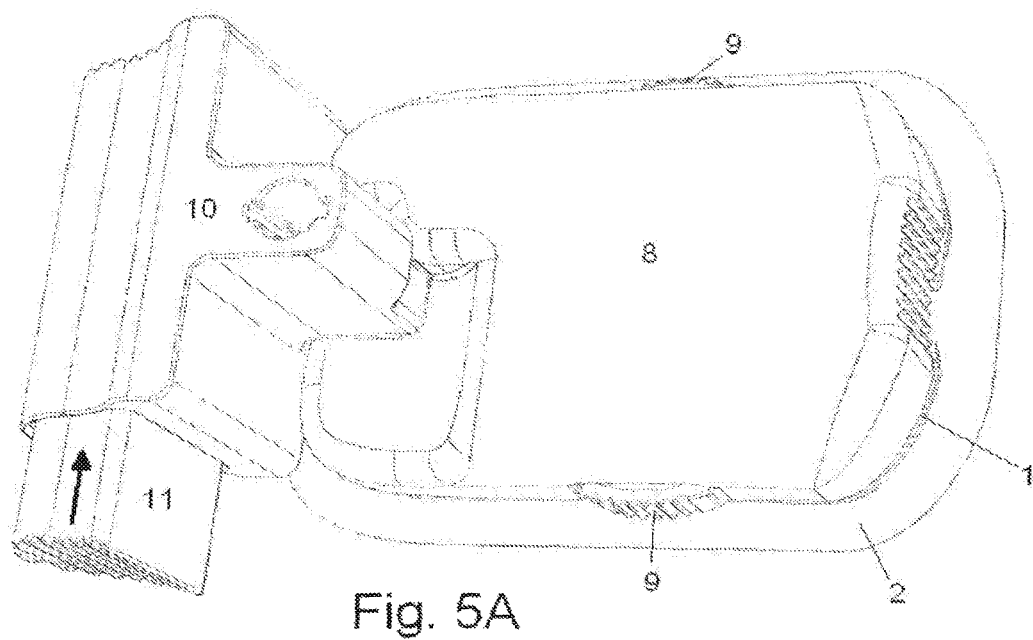
FIGS. 5A and 5B show the second embodiment of the assembly, in FIG. 5A the insertion device is mounted on the base part and in FIG. 5B the insertion device has been removed from the base part.

The FIGS. 4 and 5A and B show a second embodiment of an assembly comprising an inserter 10 according to the invention, a delivery part 8 and a base part. The base part comprises a surface plate 1 attached to a contact surface. The surface plate 1 is in this embodiment constructed of a molded plastic material and the contact surface is the proximal side of a mounting pad 2 which mounting pad 2 is unreleasably fastened to the surface plate 1 during manufacturing of the device. "Proximal" means the side or surface closest to the patient when the mounting pad is adhered to the patient, "distal" means the end or surface furthest away from the patient when the device is in a position of use.

FIG. 4 shows the embodiment of the assembly seen from the side and FIG. 5 shows the same embodiment seen from above. The penetrating member of this embodiment is comprised in a cannula part 7 which is inserted into an opening 12A of a connector part 3 of the base part, this cannula opening 12A provides and opening which extends right through the base part. The cannula part 7 is provided with a penetrating member in the form of a cannula 22 which will penetrate the surface of the skin of the patient during the insertion and be positioned sub- or transcutaneously.

The inserter 10 holds the cannula part 7 before insertion and the insertion is initiated by pushing a handle 11. FIG. 5 shows the direction the handle 11 has to be pushed in order to initiate insertion of the cannula part 7. After insertion a not shown insertion needle can be retracted to the inside of the inserter 10, afterwards the inserter 10 can be removed from the base part, leaving an inserted cannula 22 fastened to the surface plate 1. If the cannula 22 of the cannula part 7 is a hard self penetrating cannula there will be no separate insertion needle and therefore no need to retract the insertion needle.

The connector part 3 is kept in position by the surface plate 1. According to one embodiment the surface plate 1 and at least an outer cover of the connector part 3 is simply molded in one piece during manufacturing of the device. The connector part 3 forms a fluid path between e.g. a reservoir 6 of medication or a reservoir for liquid collected from the patient and a cannula part 7. Therefore the connector part 3 is provided with at least two openings, one opening at each end of the fluid path where the first opening 13 is an inlet or outlet opening receiving or delivering fluid to a reservoir 6 and the second opening 12 is an inlet or outlet opening receiving or delivering fluid to a cannula part 7 (see FIG. 6C-D). The connection part 3 might be provided with extra openings e.g. for injection of a second medication or nutrient or for letting the fluid in the fluid path get in contact with a sensor. In order to secure a fluid tight connection between the outlet opening 12 in the connection part 3 and the cannula part 7 the outlet opening 12 of the connection part 3 is provided with an elastic sealing 18 around the outlet opening 12. When the cannula part 7 is inserted it will be press fitted into the cannula opening 12 and the elastic sealing 18 will provide a completely fluid tight gasket around the corresponding openings 12 and 20. In order to improved the press-fitting and thereby the fluid tight connection between the cannula part 7 and the outlet of the fluid path, the cannula opening 12A can be provided with a decreasing cross-section in a plane parallel to the cannula 22 when inserted and perpendicular to the surface where the outlet of the fluid path is positioned. The cannula part 7 will have a corresponding decreasing cross-section.

In the following the first opening 13 will be referred to as "inlet" and the second opening 12 will be referred to as "outlet" although the direction of the flow through the fluid path is not significant for the invention.

The connection part 3 is further provided with a cannula opening 12A which accurately fits around a cannula part 7 i.e. the cannula opening 12A has the same shape or profile as the cannula part 7 and is just big enough to let the cannula part 7 pass through and then fit into the opening. When the cannula part 7 is fully inserted into the base part and the patient, then the upper surface i.e. the distal surface of the cannula part 7 is normally at level with or at a lower level than the outer surface of the connection part 3 surrounding the cannula opening 12A. When the cannula part 7 has been fully inserted into the connection part 3, then an opening 20 in a side surface of the body of the cannula part 7 corresponds to the opening 12 of the fluid path of the connection part 3 and fluid can flow from one part to the other.

Figure 5B:
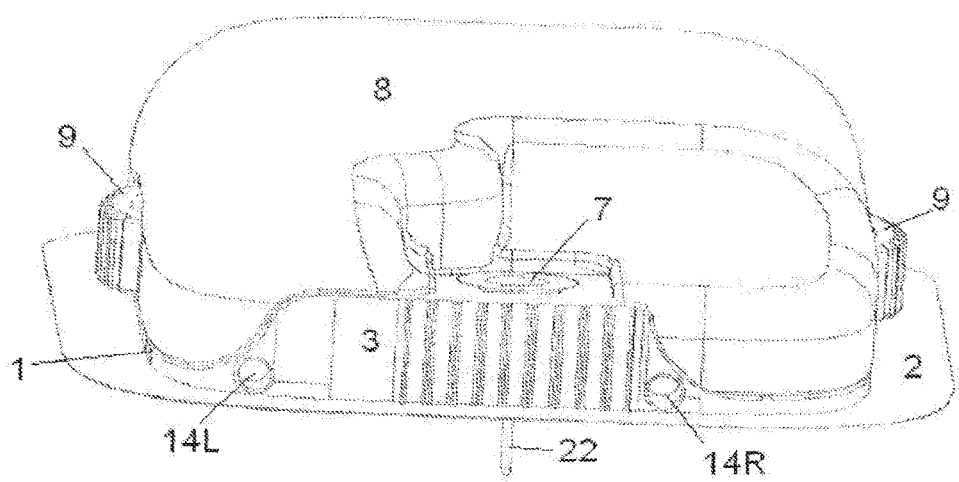

FIG. 5B shows the embodiment of FIG. 5A where the inserter has been removed. FIG. 5B shows the device from the end which was covered by the inserter 10 before it was removed. From this end it is possible to see a part of the fastening means 14 which assure attachment of the inserter 10 to the base part before insertion. According to this embodiment the fastening means 14 comprise two openings 14L and 14R in the connector part 3. These openings correspond to two protruding parts 14PL and 14PR (see FIGS. 7 and 8) which protrude from the side of the inserter housing turned towards the base part and the connector part 3 with the corresponding opening. When the fastening means 14L and 14R on the base part is engaged with the corresponding fastening means 14PL and 14PR on the inserter 10, the inserter 10 is prevented from moving in relation to the base part, at least in the direction perpendicular to the surface plate 1. After insertion of the penetrating member where the penetrating member has been fully inserted into the base part, the inserter 10 can be removed or detached from the base part. When detaching the inserter 10 from the base part, the inserter 10 is moved in a direction horizontal to the patients skin i.e. the base part is not subjected to a force perpendicular to the patients skin i.e. a force pulling the base part away from the patient. Alternatively it would be possible to e.g. glue the inserter to the delivery part 8 before insertion along adjoining surfaces between the inserter 10 and the delivery part 8 which surfaces should be essentially perpendicular to the patient's skin in order to create a pull in a direction parallel to the patients skin when the inserter 10 is removed from the delivery part 8.

Figure 6A:
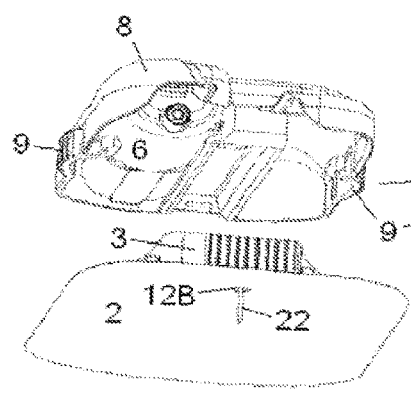
FIG. 6 shows second embodiment of the assembly without the insertion device and having the delivery part separated from the base part A: seen from below; B: seen from above; C: seen from above and showing the connection part of the base part and D: showing the base part alone seen from above.
Figure 6B:
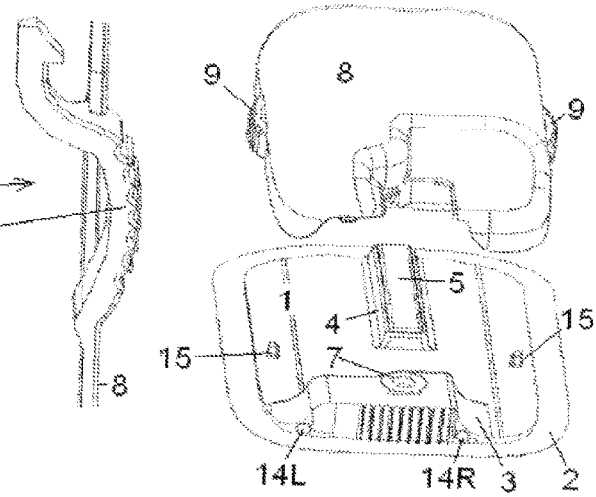
Figure 6C:
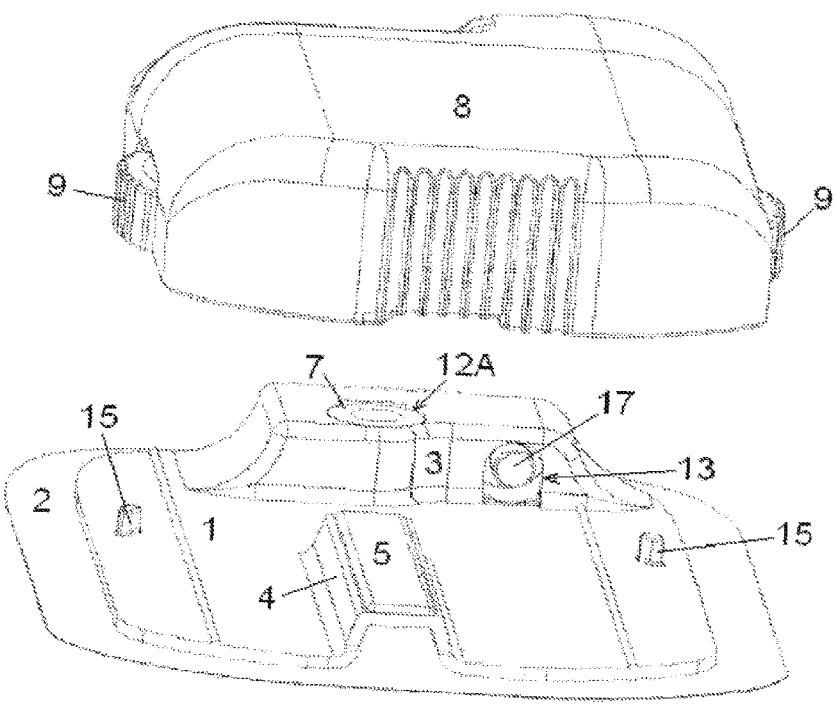
Figure 6D:
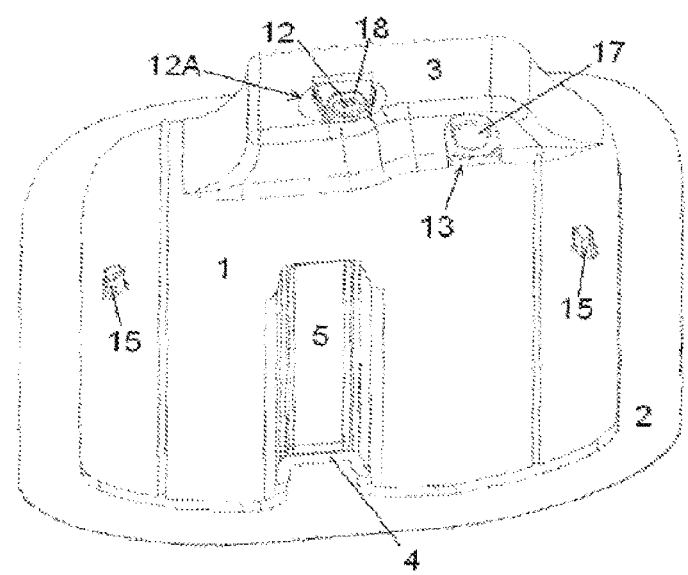

FIGS. 6A-D show the base part and the delivery part in a separated position from different angles. In FIG. 6A the two parts are shown from below. This view shows an opening 12B through which the penetrating member 7 can be inserted through the base part and through which opening 12B the cannula 22 extends. From this view it is possible to see how the reservoir 6 can be positioned in the delivery part 8 and to see how two opposite positioned release handles 9 are placed at the edge of the delivery part 8. Further a longitudinal track corresponding to longitudinal raised guiding means 4 on the base part can be seen.

The two release handles 9 are formed as s-shaped bands where one end is fastened hinge-like to the housing of the delivery part 8 and the first curve in the s-shape is slightly extending the outer surface of the housing of the delivery part whereas the second curve is free i.e. not attached to the housing of the delivery part 8 and is provided with a hook-like shape which can fold around a part 15 protruding from the distal surface of the base part. When the delivery part is locked to the base part both release handles 9 are folded round a protruding part 15, when the delivery part 8 is to be removed from the base part, the two opposite release handles 9 are pushed together whereby the hook-like parts of the release handles 9 are released from the protruding parts 15 of the base part, and the delivery part can be moved backwards i.e. in the direction away from the cannula part 7 and removed from the base part in this direction.

In FIG. 6B the two parts are shown from above. This view shows how the delivery part 8 of this embodiment can be joined to the base part by pushing the delivery part 8 down toward the guiding means 4 which in this case is a longitudinal raised platform having e.g. a metal lining 5 fastened to the top surface. The delivery part 8 is provided with corresponding means e.g. comprising a track corresponding to the raised platform 4. The corresponding means of the delivery part 8 can slide along the metal lining 5 of the raised platform 4 in the longitudinal direction. When the delivery part 8 arrives at its working position, the two release handles 9 engage respectively with the two protruding parts 15 protruding from the upper surface of the surface plate 1. When the delivery part 8 is in its working position it is locked in all horizontal directions by the release handles 9. The locking mechanisms make it possible to fasten and release the delivery device from the base part as often as needed i.e. a single-use base part can be combined with a multi-use delivery part.

In FIG. 6C the two parts are shown from the end opposite of where the inserter was fastened before insertion of the penetrating member. From this side it is possible to see the inlet opening 13 in the connection part 3 through which e.g. medication from the reservoir 6 can enter, the inlet opening 13 is protected with a membrane to prevent contamination with microorganisms. According to one embodiment the connection part 3 is provided with both a connector needle (not shown as it is placed behind the bubble shaped membrane) and a bubble shaped self closing membrane 17 and the reservoir 6 can be provided with a bubble shaped self closing membrane. Hereby a fluid path is established providing transfer of medication e.g. insulin or nutrients from the reservoir to the connector part 3. As both parts are provided with self closing membranes it will be possible to separate the two units from each other and rejoin them at a later time without the connection part 3 and thereby the patient being contaminated.

FIG. 7 shows a longitudinal cut through an assembly as shown in FIG. 4-6. From this view it is possible to the how the fastening means 14 of respectively the connector part 3 of the base part and the inserter 10 are joined together.

FIG. 8 shows the inserter 10 removed from the rest of the assembly. From this side it is possible to see the fastening means 14PR and 14PL of the inserter.

Figure 9:
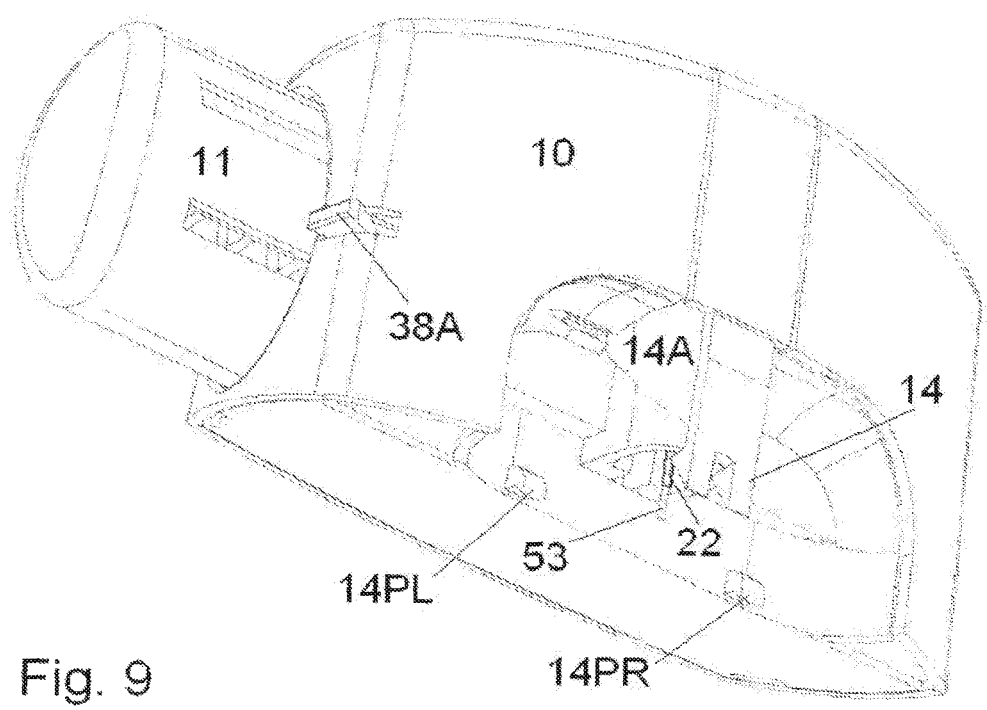
FIG. 9 shows a third embodiment of an inserter to be used with the assembly in a state before insertion of a cannula part.
Figure 10:
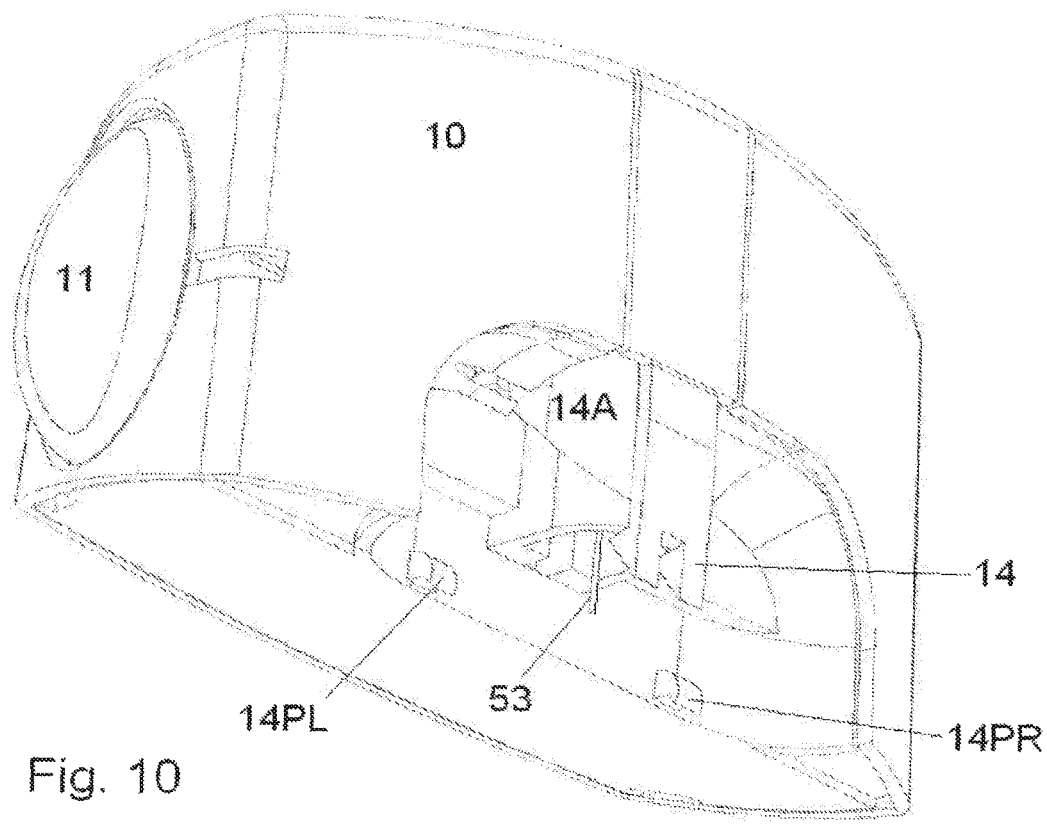
FIG. 10 shows the same embodiment of an inserter as FIG. 9 after insertion of a cannula part.

FIGS. 9-11 show a third embodiment of an inserter, in FIGS. 9 and 10 the inserter is shown separated from the rest of the assembly. The inserter 10 comprises like the first and second embodiment of the inserter an actuator handle 11 which in FIG. 9 is shown in a pre-insertion state and in FIG. 10 is shown in an after-insertion state. The third embodiment of the inserter is provided with a moving part 38 as shown in FIG. 12 and this moving part is provided with a protruding member 38A which is an integrated part of the moving part 38. The moving part 38 is shown two different views in FIGS. 12A and 12B. That it is "an integrated part" means that it moves simultaneously with the moving part and is positioned stationary in relation to the moving part. Normally it will be molded together with the moving part and be of the same material, but it can also be made of a different material and attached to the moving part 38 after the moving part 38 has been produced.

The protruding part 38A on the moving part 38 is provided with a ramp. The ramp is an inclined surface placed on the forward side of the protruding part 38A in such a way that the front profile of the protruding part 38A forms an arrowhead.

The fastening means of this embodiment comprises a hinged part 14 which in this embodiment is fastened to the housing of the inserter 10, the hinged part could alternatively be fastened to an internal part of the inserter e.g. the same part as the protruding parts 14PL and 14PR is fastened to. In the shown embodiment the hinged part 14 is actually made as a part of the housing as the hinged part 14 is created by making two cuts in the full height of the housing. The housing is normally made of a hard, molded plastic such as polypropylene and the relatively long shape of the hinged part 14 makes it very flexible i.e. the hinged part 14 is very pliant and it will be easy to push it outward from the relaxed position, the inward movement is blocked by the presence of the guiding means 33 for the penetrating member which in this embodiment is a cannula part 7. The hinged part 14 can also be made of a material which is different from the material of the housing of the inserter e.g. metal which are then attached to the housing in a rotatable manner.

The hinged part 14 is provided with two inward hooks ("inward" means that the hooks point toward the inside of the housing) at the lower or proximal end of the hinged part 14 and the two hooks lock the housing to the base part by catching a stationary protruding part 14B of the base part. As the two hooks are turned inward they are released from their locked position by being pushed outward i.e.

away from the centre of the housing. The hinged part 14 is also provided with a contact member 14A having the form of a rounded plate of a rigid material placed inwards from the hinged part 14 around the guiding means 33 for the cannula part 7. When the moving part 38 moves from its start position to its end position the protruding member 38A which is placed on the trailing edge of the moving part 38 will hit the contact member 14A with the ramp surface and the contact member 14A will be forced outward and so will the hinged part 14 as the contact member 14A is attached unreleasably and rigidly to the hinged part 14.

The housing of the inserter also comprises two protruding parts having the form of rounded hooks 14PL and 14PR on the inside surface of the wall opposite the inward hooks of the hinged part 14. These protruding parts 14PL and 14PR fits into corresponding openings 14L and 14R of the base part close to the connector part 3. The openings in the base part are shown in FIG. 16A. When the fastening means in the form of the openings 14L and 14R on the base part is engaged with the corresponding fastening means in the form of the rounded hooks 14PL and 14PR on the inserter 10, the inserter 10 is prevented from moving in relation to the base part, both in the direction parallel to the longitudinal direction of the base part as the protruding parts are rounded and form a grip around the opening, and also in the direction perpendicular to the surface plate 1 due to the insertion of the protruding part into the opening. After having fully inserted the penetrating member (FIG. 10), the inserter 10 can be removed or detached from the base part.

In order to detach the inserter 10 from the base part, the inserter 10 is pivoted around an axis provided along the upper surface of the openings 14L and 14R. The upper (distal) surface of the openings 14L and 14R provide a contact surface for the rounded hooks 14PL and 14PR along which contact surface the downward contact surface of the rounded hooks 14PL and 14PR can slide and thereby be forced out of the openings 14L and 14R when subjecting the inserter housing 30 to a rotational movement. After insertion the base part comprising the surface plate 1 and the inserted part 7 is completely stationary in relation to the surface in which the cannula or sensor has been inserted and the rotational movement is only provided by the inserter 10.

The rotatable movement is made possible at the lower or proximal surface of the housing of the inserter is inclined in relation to the upper surface 1 of the base part and therefore leaves room for the displacement of the housing 30, at the end of the rotational movement the lower (proximal), inclined surface of the inserter housing will normally rest against the patients skin.

Figure 11A:
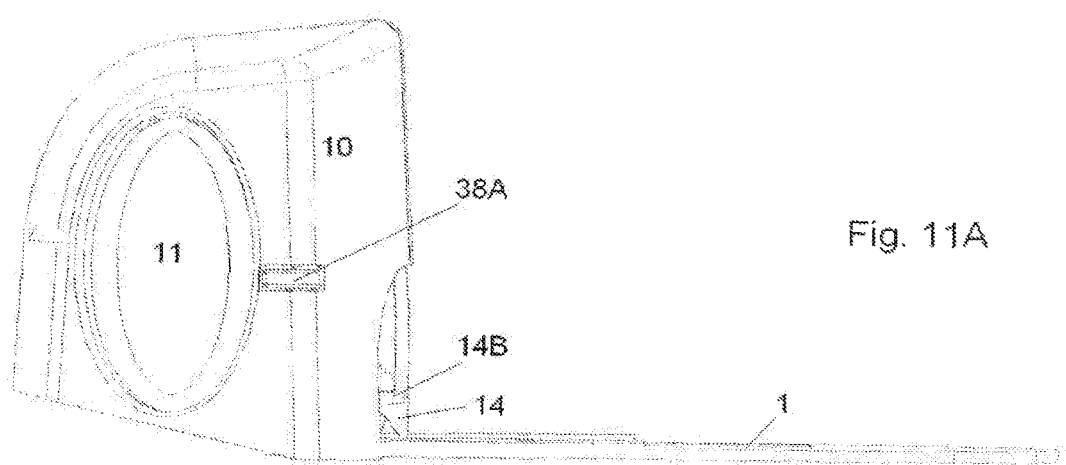
FIGS. 11A-C show how the embodiment of the inserter shown in FIGS. 9 and 10 are being detached from a base part of an assembly according to the invention.
Figure 12A:
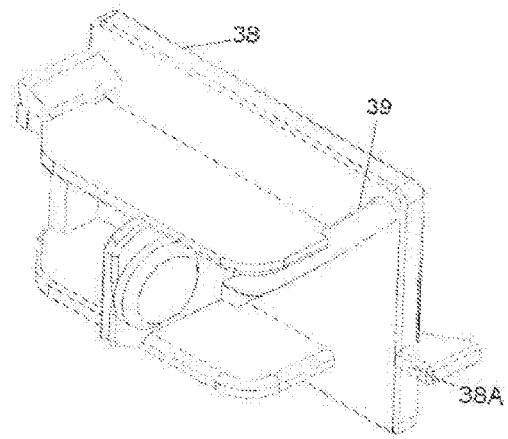
FIGS. 12A and 12B show an embodiment of a moving part to be used with an assembly as shown in FIG. 9-11.
Figure 12B:
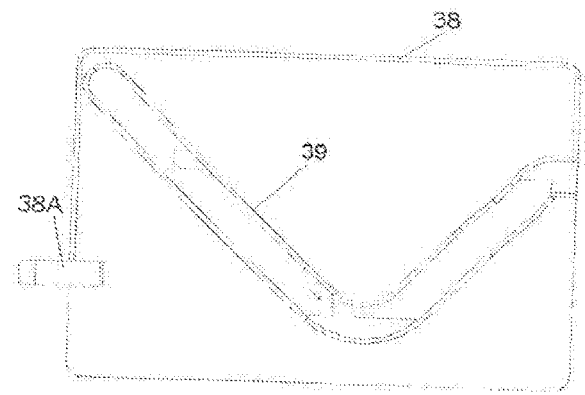

FIG. 11A shows the inserter in a position before insertion. In this state the inclined lower surface is lifted away from the patient's skin. The inward hooks of the hinged part 14 are locked around the protruding part 11 B on the base part.

Figure 11B:
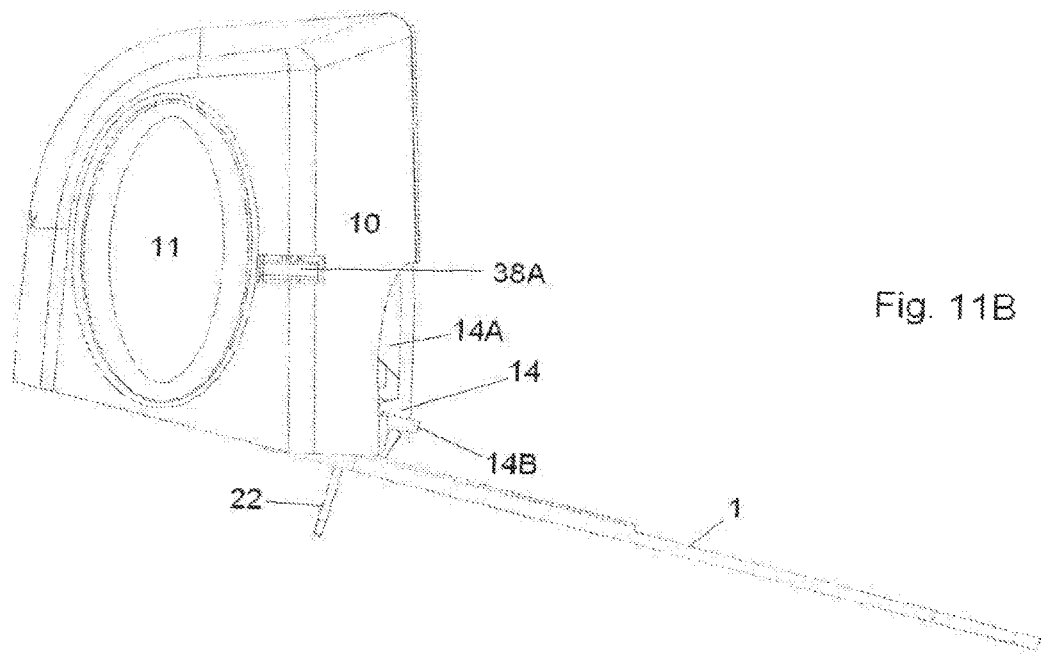

FIG. 11B shows the inserter after the cannula part has been inserted. In this state the inclined lower surface is parallel to the patient's skin and the inward hooks of the hinged part 14 have been released from the locked position.

Figure 11C:
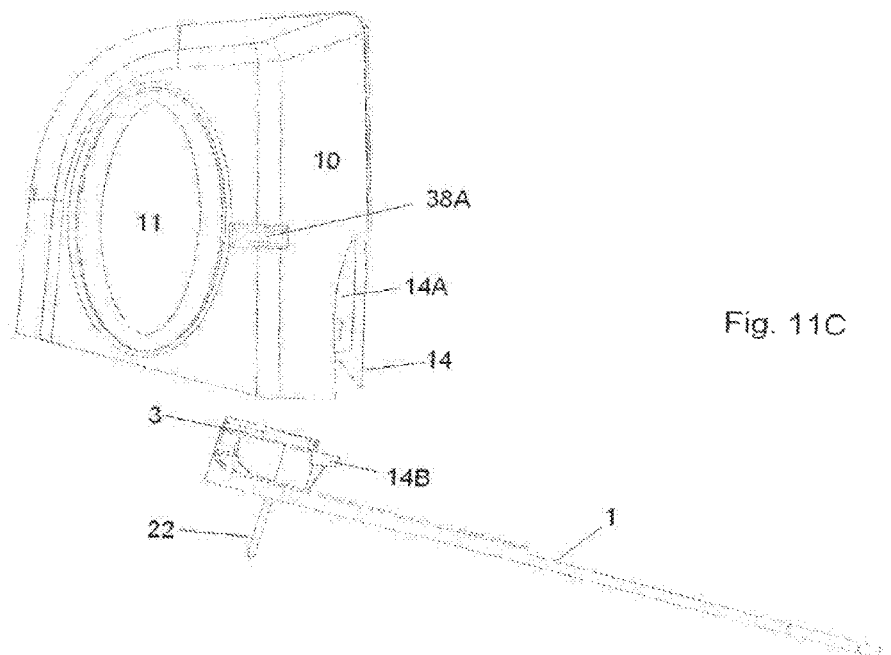

FIG. 11C shows the inserter after it has been removed from the base part.

FIGS. 12A and 12B show the moving part 38 of the third embodiment of the inserter shown in FIG. 9-11. FIG. 12A shows the "back side" i.e. the side turned away from the penetrating member and FIG. 12B shows the "front side" i.e. the side turned toward the penetrating member. The figures show the protruding part 38A placed at the trailing edge of the moving part 38 having the inclined side i.e. the ramp facing forward in the direction of movement, and the figures show the transformation means 39 in the shape of a longitudinal opening formed as a V where the start position is at the upper end of the first line in the V and the end position for the penetrating member is at the upper end of the second line in the V.

Figure 13A:
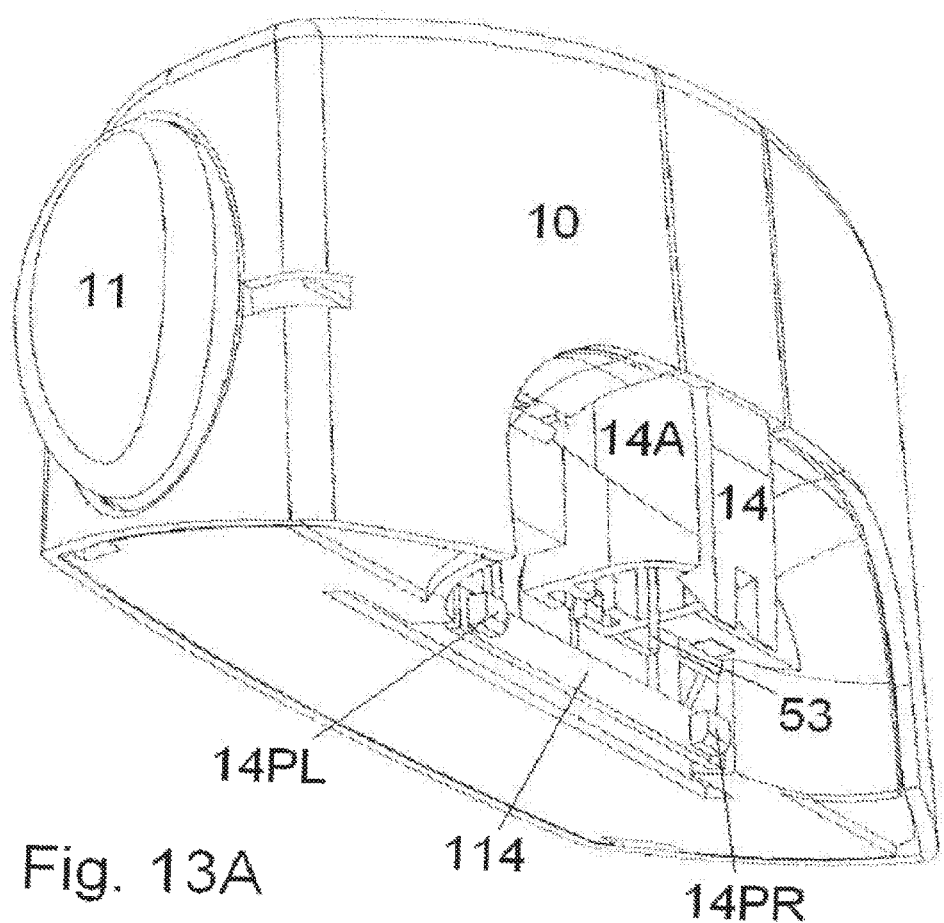
FIGS. 13A and 13B show a fourth embodiment of an inserter to be used with the assembly in a state after insertion of a cannula part.
Figure 13B:
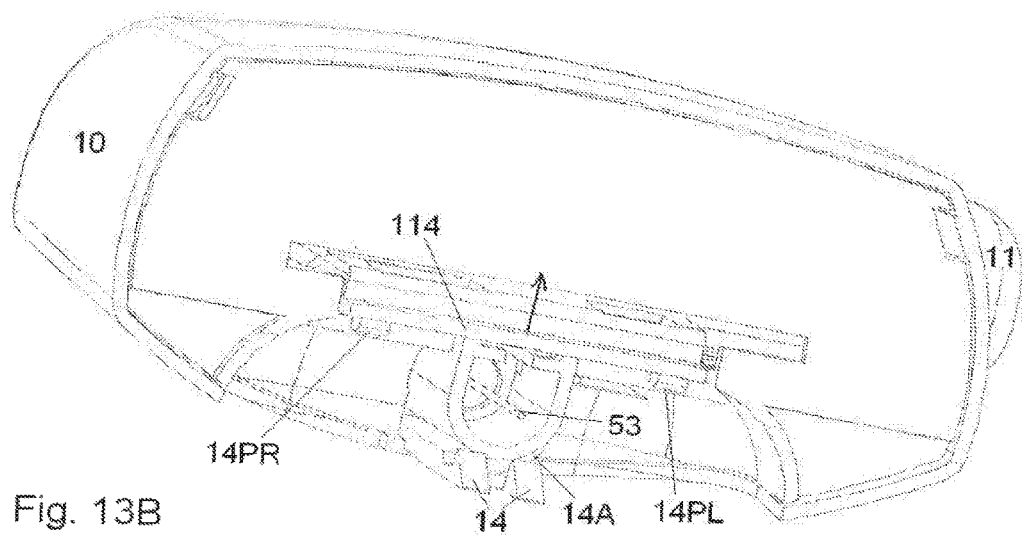

FIGS. 13 and 14 show a fourth embodiment of an inserter, this embodiment differs from the third embodiment by the fastening means 14 securing the inserter to the base part. The inserter 10 is in FIGS. 13 and 14 shown in an after-insertion state where it has been removed from the base part. The fourth embodiment has means to release to sets of functionally independent fastening means which are supporting each other.

Like the third embodiment the fourth embodiment of the inserter is provided with a moving part 38 (see FIGS. 15A and 15B) having a protruding member 38A being an integrated part of the moving part 38. The moving part 38 of the fourth embodiment is further provided with a second integrated part called the positioning means 27. These positioning means 27 are attached to the lower trailing edge of the moving part 38.

The fastening means of this embodiment comprises like the third embodiment of the inserter a hinged part 14 which is fastened to the housing of the inserter 10 and the hinged part 14 moves in the same way as described for the third embodiment of FIGS. 9 and 10. The hinged part 14 of the fourth embodiment is also provided with two inward hooks at the lower or proximal end of the hinged part 14. The two hooks lock the housing against the base part by catching a stationary protruding part 14B of the base part having a downward or proximal contact surface. As the two hooks are turned inward they are released by being pushed outward i.e. away from the inside of the housing.

The hinged part 14 is also provided with a contact member 14A having the form of a plate placed in a direction toward the centre of the inserter i.e. "inwards" from the hinged part 14 around the guiding means 33 for the cannula part 7. When the moving part 38 moves from its start position to its end position the protruding member 38A which is placed on the trailing edge of the moving part 38 will hit the contact member 14A with the ramp surface of the protruding member 38A and the contact member 14A will be forced outward and so will the hinged part 14 as the contact member 14A is attached unreleasably and rigidly to the hinged part 14.

According to the fourth embodiment the protruding members 14PL and 14PR are positioned on a flexible member 114. The protruding members 14PL and 14PR according to this embodiment have a rectangular profile but could also have e.g. a round or triangular profile. The protruding members 14PL and 14PR fits into openings 14P and 14L of the base part close to the connector part 3. These openings correspond to the rectangular protruding members 14PL and 14PR. When the fastening means in the form of the openings 14L and 14R on the base part are engaged with the corresponding fastening means in the form of the protruding members 14PL and 14PR on the inserter 10, the inserter 10 is prevented from moving in relation to the base part, both in the direction perpendicular to the surface plate 1 and in any direction parallel to the surface plate 1.

The flexible member 114 is attached to the housing or a part being stationary in relation to the housing 30 in such a way that the flexible member can move between two positions, a first position where the inserter is locked to the base part, and a second position where the inserter is released from the base part. Both FIGS. 17A and 17B show the flexible member 114 in a relaxed locked position and an arrow in FIG. 17B indicates the direction it moves in, in order to get to the second released position. According to the shown embodiment the flexible member 114 is made as an integrated part of the guiding means 32 for the moving part i.e. the flexible member 114 constitutes a part of the surfaces or walls along which the moving part 38 slides. The flexible member 114 is provided with a contact part 115 which according to this embodiment has a triangular profile with the sharpened edge pointing forward in the direction of movement during insertion. The contact part 115 is formed with a ramp shaped surface pointing in the direction opposite of the direction of movement of the moving part 38 during insertion.

In order to bring the flexible member 114 from a first relaxed and locked position into a second and released position the flexible has to be subjected to a force large enough to be able to move the flexible member 114 to the second position.

Figure 14A:
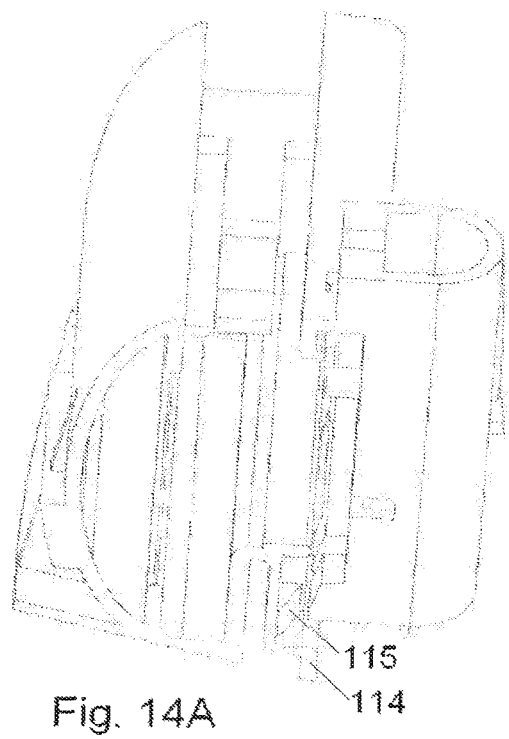
FIGS. 14A and 14B show the internal parts of the inserter housing of the fourth embodiment of the inserter.
Figure 14B:
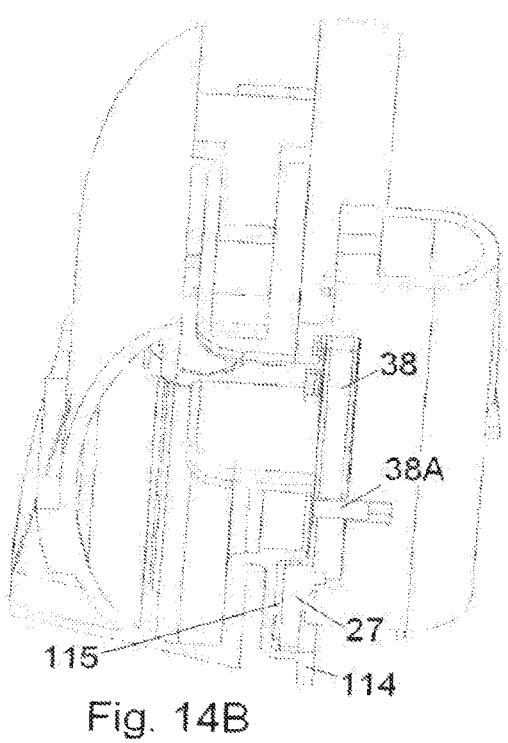

FIGS. 14A and 14B shows the internal parts of the inserter housing 30 which provide the guiding parts for the moving part and which are not visible when the surrounding housing is in place. FIGS. 14A and 14B show identical cuts through these internal housing parts but in FIG. 14A the moving part 38 is removed in order to make the contact part 115 of the internal parts visible. The contact part 115 consists of a protruding ramped surface which will get in contact with the positioning means 27 of the moving part 38 when the moving part 38 is in its end or final position.

Figure 15A:
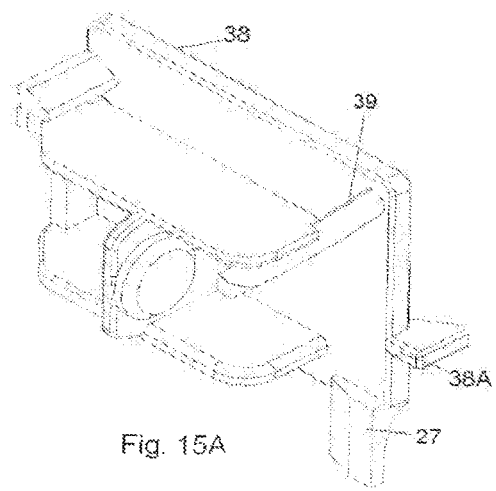
FIGS. 15A and 15B show an embodiment of a moving part to be used with an assembly as shown in FIG. 13-14.
Figure 15B:
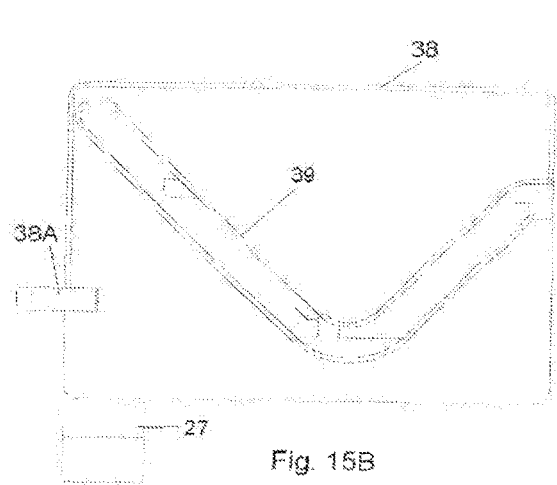

FIGS. 15A and 15B show the moving part 38 of the fourth embodiment of the inserter shown in FIG. 13-14. FIG. 15A shows the "back side" i.e. the side turned away from the penetrating member and FIG. 15B shows the "front side" i.e. the side turned toward the penetrating member. The figures show the protruding part 38A placed at the trailing edge of the moving part 38 having the inclined side i.e. the ramp facing forward in the direction of movement, and the figures show the transformation means 39 in the shape of a longitudinal opening formed as a V where the start position is at the upper end of the first line in the V and the end position for the penetrating member is at the upper end of the second line in the V. The end position is placed lower than the start position. At the lower edge of the moving part 38 is shown positioning means 27 which assures the positioning of the moving part 38 in relation to the housing of the inserter when sliding along the guiding means 32 provided by the surrounding parts of the inserter housing but which main function is to force the flexible member 114 of the housing "backwards" when the moving part 38 and the integrated positioning means 27 passes by.

When the positioning means 27 of the moving part 38 touch the flexible member 114, the flexible member 114 is pushed away from the connection part 3 of the base part, and the fastening means in the form of the protruding parts 14PL and 14PR are pulled out of the corresponding openings in the base part 14L and 14R. When the moving part 38 is in its end position, the integrated parts 38A and 27 will be at positions where both the hinge part 14 and the flexible member are pushed away from their relaxed and locked position which means it will be possible to remove the inserter from the base part when the moving part 38 is in its end position.

Figure 2:
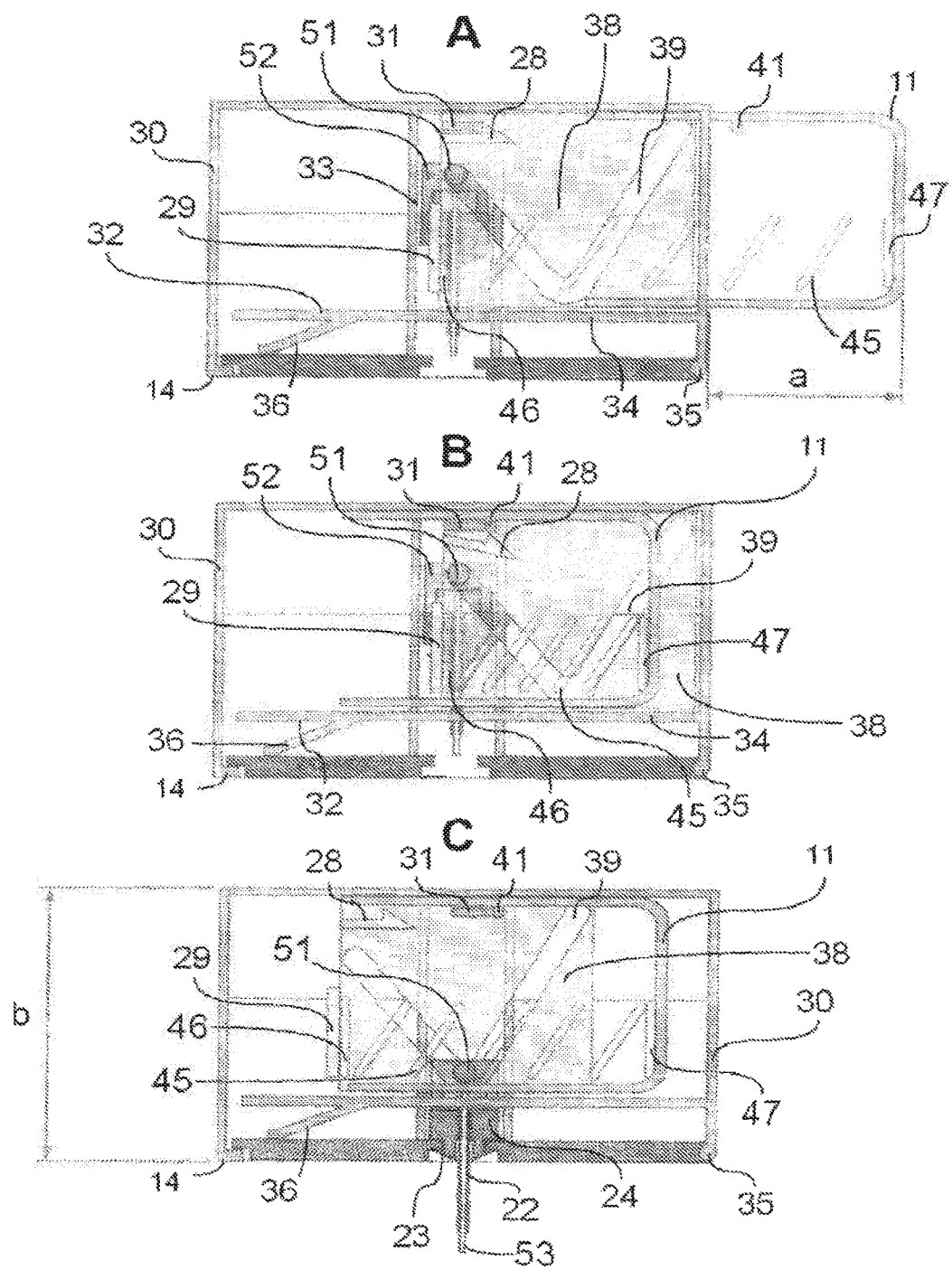
FIGS. 2A-F show a cross section of a second embodiment of an insertion device in six states. A: before activation; B: after activation, C: just after insertion, D: after retraction of insertion needle, E: after release of inserter housing and F: after removal of insertion device from base part.
Figure 2:
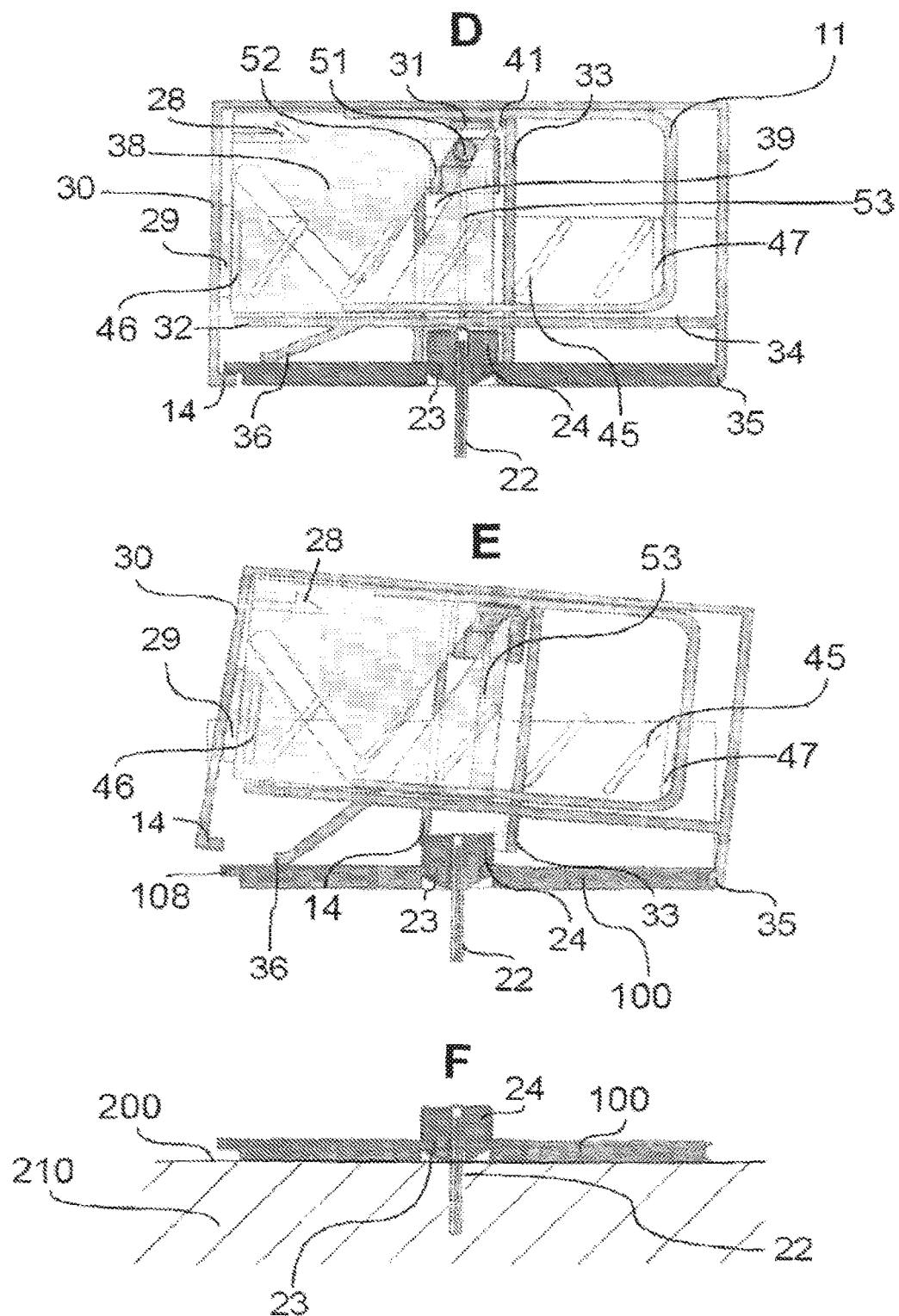
Figure 16:
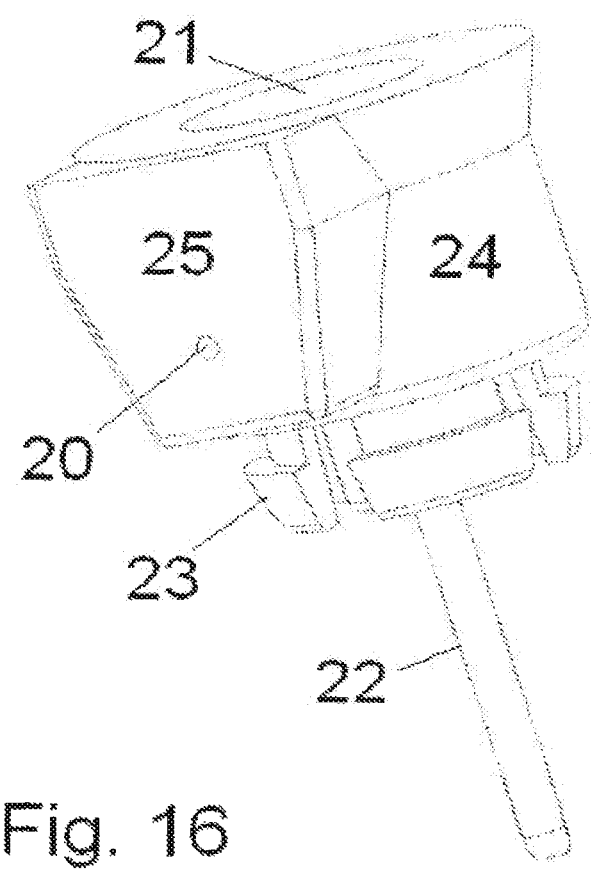
FIG. 16 shows one embodiment of a penetrating member which can be used with the assembly.

FIG. 16 shows an enlargement of a cannula part 7 used with the embodiments of FIG. 1-2. This embodiment comprises a body 24 provided with a cannula 22 and with a protruding front 25 having a flat surface provided with an opening 20. The protruding front 25 of the cannula part 7 need not be flat; it can actually have any desired shape as long as it is possible to create a corresponding surface on the connection part 3 facing the cannula part 7. In one embodiment the front 25 is inclined in such a way that the cross-section at the upper i.e. distal end of the cannula part 7 is larger than the cross-section at the proximal end of the front, i.e. the end closest to the patient after insertion. The opening 20 of the protruding front 25 is an inlet or outlet through which liquid can enter or exit the cannula part 7. The body 24 is further provided with a top opening 21 which can be covered with a self closing membrane. The opening 21 need some kind of entrance protection as it is facing an outer surface which is in contact with the surroundings. The top opening 21 is primarily used when inserting the cannula part 7 if the cannula 22 is a soft cannula. That the cannula 22 is soft means that it is made of a relatively soft material which can not by it self penetrate the patients skin, in this case it is necessary to use a pointy insertion needle of a relatively hard material when inserting the cannula and this pointy needle can be inserted through the top opening 21, pass through an inner hollow in the body 24 of the cannula part and further pass through the full length of the cannula 22 in such a way that the pointy end of the insertion needle stick out of the open end of the hollow cannula 22. After insertion i.e. after the cannula 22 has been placed sub- or transcutaneous in the patient, then the insertion needle is retracted and the cannula 22 is left inside the patient. The cannula part 7 is also provided with fastening means 23 which in this embodiment has the form of a series of outward hooks 23 which are flexibly fastened to the body 24 in such a way that the hooks can pivot inwards toward the centre of the cannula part 7. When the cannula part 7 is pressed toward the base part, the hooks 23 passes an edge which pushes them toward the centre as they passes the edge and when the hooks have passed the edge they return to their original position and as a upward surface of one or more of the hooks touch a downward surface of the edge the cannula part 7 is locked unreleasably against the edge.

Figure 17:
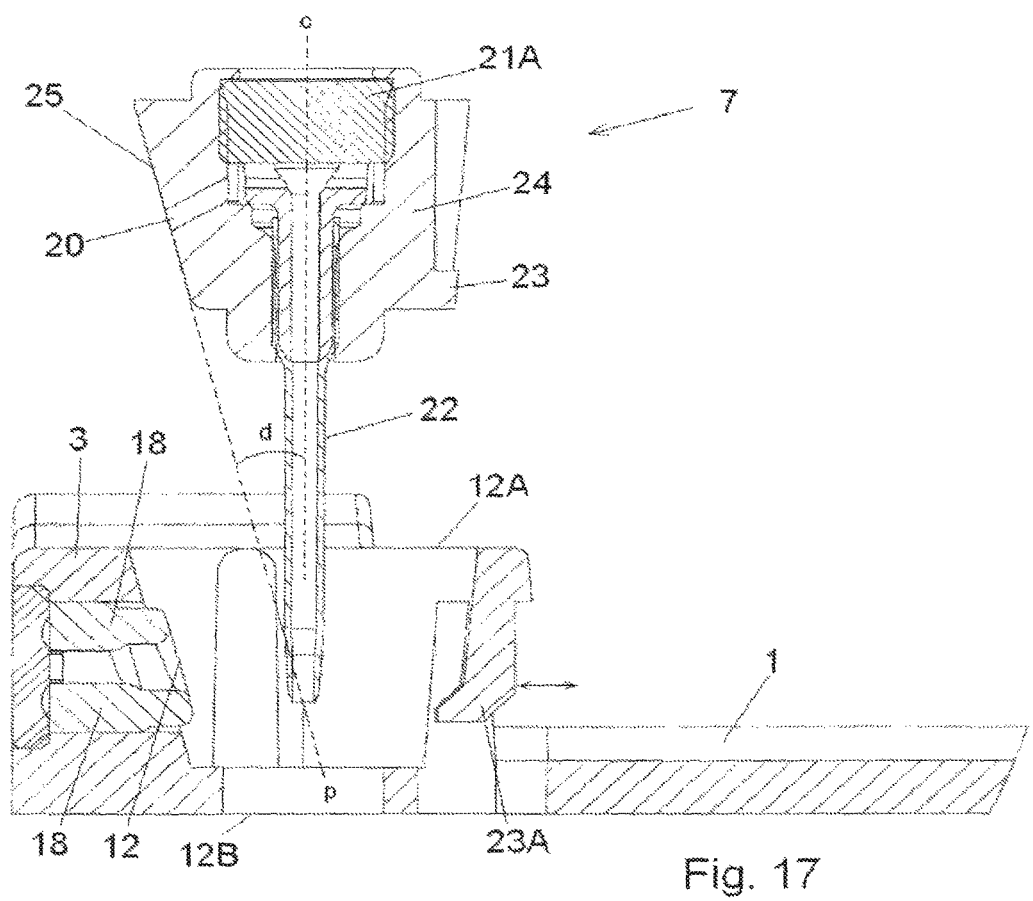
FIG. 17 shows a cut-through view of a second embodiment of a penetrating member which can be used with the assembly.

FIG. 17 shows an enlargement of a second embodiment a cannula part 7. This embodiment also comprises a body 24 provided with a cannula 22 and with a protruding front 25 having a flat surface provided with an opening 20 but according to this embodiment the protruding front 25 is inclined in order to reduce the force required to insert the cannula part and in order to reduce distortion of the sealing 18. The inclination of the front 25 is defined by the angle d between the centre line c of the cannula 22 and a line parallel to the surface around the opening 20. The angle d will be larger than 0° and smaller than 90°, normally d $\in ]0°, 30°]$ depending on the diameter of the sealing 18 or $[60°, 90°[$. The distance $d_1$ between at the distal end of the surface of the protruding part 25, i.e. the end of the cannula part 7 which is furthest away from the patient after insertion, and the centre c of the cannula part 7 is larger than the distance $d_2$ between the surface of the protruding part 25 at the proximal end, i.e. the end closest to the patient after insertion, and the centre c of the cannula part 7. Normally the distance $d_2$ will be so small that the proximal end of the protruding front 25 does not touch the sealing 18 of the connection part 3 during insertion.

In one embodiment (not shown) the angle d is close to 90° i.e. d=90°, such an embodiment would in a drawing corresponding to FIG. 11 appear to have an upward opening 12 of the connection part 3 fitting to a downward opening 20 of the cannula part 7. This means that the force pushing the cannula part 7 toward the sealing 18 will be close to perpendicular to the contact surface of the sealing 18 and this will prevent that the sealing is distorted during insertion of the cannula part 7 by the cannula part 7 sliding along the sealing 18. In another embodiment (shown in FIG. 16) d=0° as the protruding front 25 and the centre line c are parallel. According to this embodiment the cannula part 7 will be in sliding contact with the protruding sealing 18 which can cause the sealing to be distorted.

As according to the embodiment of FIG. 16 the protruding front 25 of the cannula part 7 need not be flat; it can actually have any desired shape as long as it is possible to create a corresponding surface on the connection part 3 facing the cannula part 7. Also the opening 20 of the protruding front 25 can be an inlet or an outlet depending on the purpose of the cannula part 7. In FIG. 17 which is a cut-through view it is shown how the top opening 21 of the body 24 is covered with a self closing membrane 21A. As according to the embodiment of FIG. 10 the top opening 21 is primarily used when inserting the cannula part 7 if the cannula 22 is a soft cannula but the top opening 21 can also be used to inject medication or nutrients other than the primary medication which could be e.g. insulin which the patient receive via the opening 20.

This embodiment of the cannula part 7 is also provided with fastening means 23 and in this embodiment the fastening means 23 has the form of a protruding part 23 on the cannula part 7 which corresponds to a flexible part 23A on the stationary base part. The flexible part 23A can be pushed outward as indicated with an arrow at FIG. 17 when the protruding part 23 on the cannula part 7 passes during insertion of the cannula part 7. After insertion the upward surface of the protruding part 23 of the cannula part 7 will be locked by the downward surface of the flexible part 23A of the base part and it will not be possible to detach the cannula part 7 from the base part.

Figure 18A:
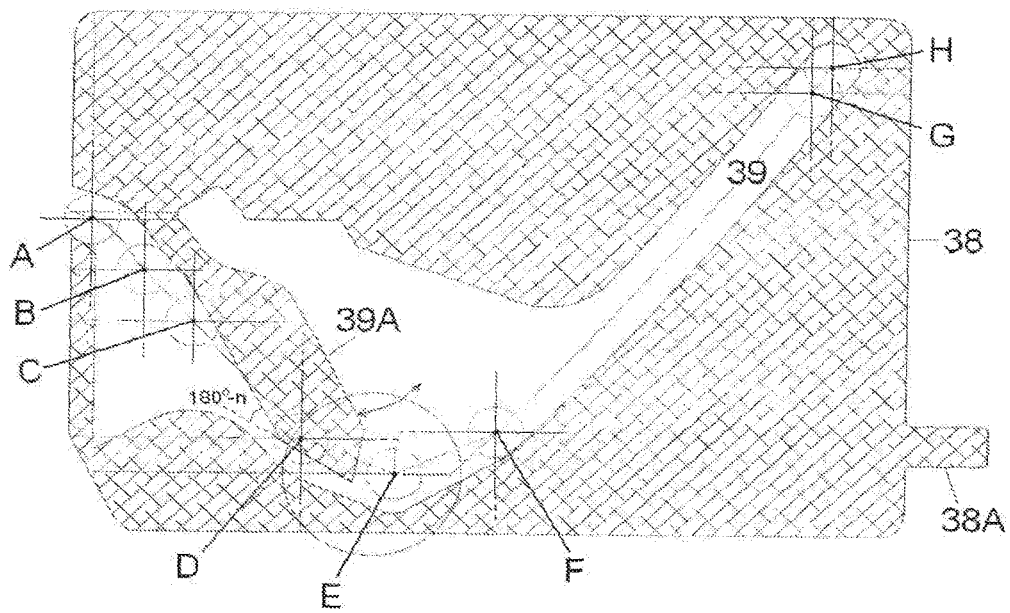
FIG. 18a shows an embodiment of a moving part having an increased tolerance.

FIG. 18a shows another embodiment of the moving part 38 which moving part has an increased tolerance for deviations from the standard insertion depth. FIG. 18a shows the "back side" i.e. the side turned away from the penetrating member and when placed in an inserter the moving part would moved from the right to the left while the penetrating member of the inserter stays in a stationary horizontal position in which position it moves first down and then up. The figure shows the protruding part 38A placed at the trailing edge of the moving part 38, and the guiding means 39 for the transformation means placed within the boundaries of the moving part. According to this embodiment the guiding means 39 are defined by a cut-out having an outer limit encircling an open space in which the transformation means 51 of the penetrating member can move. The guiding means 39 also comprise a pivotable part 39A which part can pivot around a stem through which is fastened to the body of the movable part 38. The pivotable part 39A provides a flexible upper limit as the movable part 38 moves from the right to the left according to FIG. 18a i.e. the pivotable parts 39A swings upwards as the transformation means passes. When the pivotable part 39A has passed the transformation means 51 of the penetrating member it swings back into its resting position.

The transformation means 51 has a start position relative to the movable part 38 at position A. As the movable part 38 moves to the left, the transformation means 51 of the penetrating member arrive at position B by sliding along the upper surface of the guiding means 39, at position B the insertion needle 53 of the penetrating member touches the skin of the patient.

At position C the cannula 22 which is joined to or surrounding the insertion needle 53 touches the skin of the patient.

At position D the sealing start i.e. contact is made between the cannula part 7 and the surface plate 1, and a retention click can be heard as an information to the user that the cannula 22 is in its correct position and that the retention means 23 on the stationary base part has locked the cannula part 7 to the base part.

As the transformation means 51 of the penetrating member passes from position A to position D it slides along the lower contact surface of the pivotable part 39A. This contact surface drives the penetrating member down and it is therefore important that the surface is smooth and provides as little frictional resistance as possible.

At position E the penetrating member should be fully inserted. That the pivotable part 39A can flex allows for the insertion depth to vary slightly i.e. within the range of ±0.5 mm.

At position G the insertion needle 53 is clear of the self closing membrane 21A which might cover the top opening 21 of the cannula part 7 and at position H the insertion needle is in a safe position i.e. the insertion needle 53 is retracted relative to the housing of the inserter. Normally it will be retracted at least 1 mm relative to the housing.

As the transformation means 51 of the penetrating member passes from position E to position H it slides along the upward contact surface of the trail which forms the guiding means 39 of the moving part 38. This contact surface drives the penetrating member back up and it should be smooth and provide as little frictional resistance as possible.

Figure 18B:
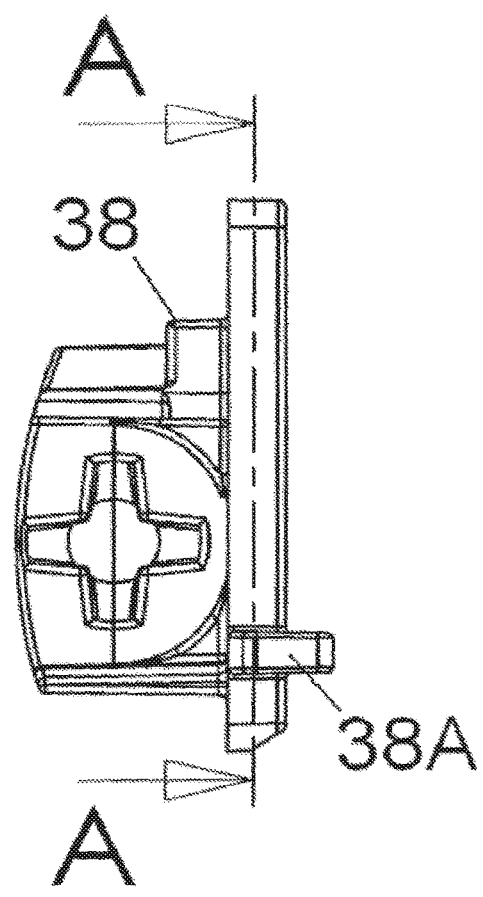

FIG. 18b shows a view of the moving part 38 seen from the side. The arrows marked A indicate the side shown in FIG. 18a.

Figure 19A:
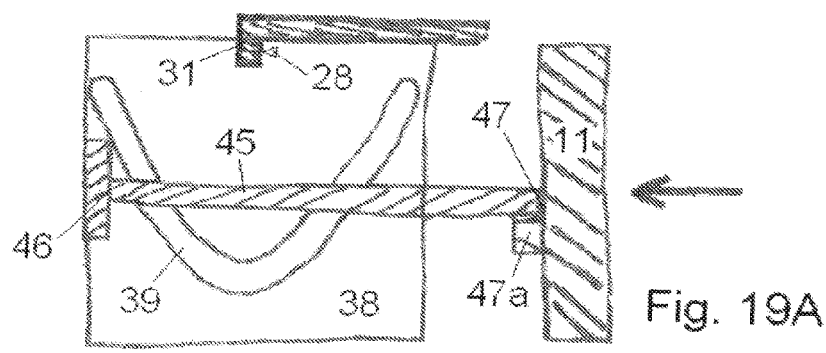
FIG. 19 shows a driving mechanism comprising a flat spring which can be used to drive the moving part forward in any of the illustrated embodiments of the inserter

FIGS. 19A, B and C show an embodiment of a flat spring which can be used to drive the moving part forward in any of the illustrated embodiments of the inserter. According to this embodiment a spring 45 is provided between the moving part 38 and the activation part 11. Normally the spring 45 will be in a relaxed state during storing as this will normally prolong the time the product can be stored while still being fully functional, if the spring 45 is in a biased state during storing there is a risk that the performance of the product will rapidly decrease. In this embodiment the spring 45 is a flat spring e.g. made of plastic material comprising two ends: a first end 46, attached to, or placed in connection with the moving part 38 and a second end 47 attached to, or placed in connection with the activation part 11. The second end of the spring 45 rests on a block 47a.

The spring 45 of the illustrated embodiment stores energy from the actuation of the of the activation part 11 as the spring 45 is biased through this first movement. A characteristic feature of a flat spring is that when the spring is biased it is bending describing a curve, the presence of the block 47a and the form of the block i.e. the length of the block 47a ensures that the spring 45 can only bend in one direction when it is biased. The not shown housing of the inserter comprises retention means 31. The retention means 31 can have the form of a pivoting arm holding the moving part 38 in a start position by engaging with locking means 28 on the moving part 38. The locking means 28 according to the embodiment illustrated in FIGS. 19A-C has the form of protruding part with e.g. a triangular or round profile.

The deformation of the spring 45 due to biasing can be used to release the moving part 38 from the locked start position.

FIG. 19A shows the embodiment in a start position. The spring is relaxed i.e. unbiased and the retention means 31 of the housing is in a locking position. In order to begin insertion it is necessary for the user o push the actuator 11, by doing this the spring will become biased. During actuation of the activation part 11 the moving part 38 is stationary.

Figure 19B:
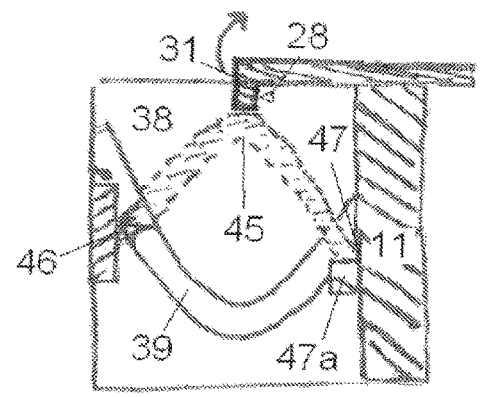

FIG. 19B shows the embodiment in a loaded position. The spring 45 is fully biased and in this fully biased state the spring 45 is curved to such a degree that it touches the retention means 31 of the housing and pushes them away from the locking means 28 of the moving part 38 thereby releasing the moving part 38 from the housing.

Figure 19C:
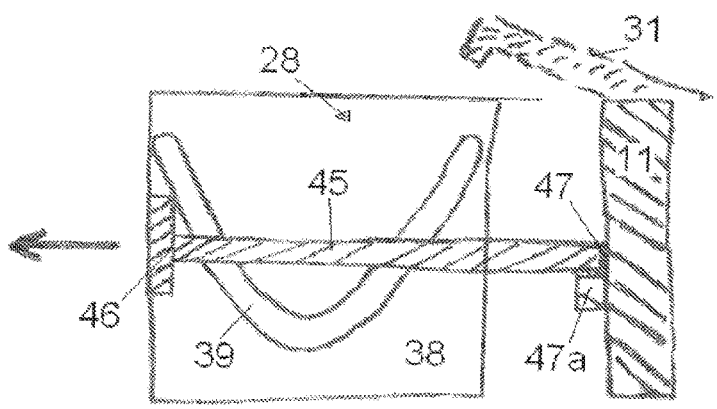

FIG. 19C shows the embodiment in a state where the moving part 38 has been moved to its end position. The actuator handle 11 is in the same position as in the fully loaded state of FIG. 19B and the retention means 31 of the housing is in an unlocking position. In this state the penetrating member which was to be inserted will be inserted subcutaneously and the next step for the user will be to remove the inserter housing from the insertion site.

The invention claimed is:
1. An insertion device comprising
    a penetrating member comprising an insertion needle connected to transformation member, the penetrating member before and during insertion is attached to a body holding a cannula or sensor at a surface of insertion after insertion has taken place,
    a moving part comprising a first guide member, the first guide member is configured to restrict the movement of the transformation member and guide the penetrating member from a first to a second position in a first direction, the first direction is linear and towards an injection site, and
    a stationary housing comprising a second guide member configured to restrict the movement of the moving part, the second guide member of the housing is configured to guide the moving part in a second direction which is linear and substantially parallel to a surface on which the stationary housing is mounted during insertion, wherein the insertion device further comprises a well-defined tube that restricts the movement of the penetrating member to a linear movement in the first direction, and wherein the transformation member of the penetrating member is movable in or along the well-defined tube.

2. An insertion device according to claim 1, wherein the housing comprises a retention member retaining the moving part in a start position, the moving part comprises a locking member interacting with the retention member in the start position and an activation part comprises a protrusion interacting with the locking member upon activation.

3. An insertion device according to claim 2, wherein a base part is fastened to a mounting surface and the insertion device comprises a fastener adapted to fasten the insertion device to the base part before insertion and to release the insertion device to the base part upon insertion of the cannula.

4. An insertion device according to claim 3, wherein the fastener comprises:
fastening members releasably locking the housing of the insertion device to the base part, and
release members releasing the housing from the base part after insertion of the penetrating member.

5. An insertion device according to claim 4, wherein the fastening members are flexibly connected to the stationary housing.

6. An insertion device according to claim 5, wherein the moving part is provided with one or more protruding parts that contact with the flexibly connected fastening members and through this contact release the insertion device from the base part.

7. An insertion device according to claim 4, wherein the release members comprise an elastic member in a biased or distorted state which upon release of the fastening member pushes the housing of the insertion device away from the base part.

8. An insertion device according to claim 2, wherein the locking member comprises a hook provided with an inclined surface pointing in a direction opposite to the forward movement of the activation part and the retention member of the housing comprises a part protruding from the housing and is adapted to interact with the hook.

9. An insertion device according to claim 2, wherein the forward movement of the activation part is stopped through contact between the protrusion of the activation part and the retention member for the moving part.

10. An insertion device according to claim 1, wherein the insertion device before insertion of the penetrating member is attached to a base part, the base part can be fastened to the surface where the penetrating member is to be inserted and the penetrating member is brought in contact with or passes through the base part upon insertion.

11. An insertion device according to claim 10, wherein the penetrating member is attached to the body holding the cannula, the body comprising a retention member securing the body and the cannula at the surface of insertion, the retention member interacts with a connector on the base part upon insertion and retains the body of the penetrating member to the base part.

12. An insertion device according to claim 1, wherein the first guide member of the moving part comprises a groove in which the transformation member of the penetrating member can slide.

13. An insertion device according to claims 12, wherein the groove is substantially V-or U-shaped defining a starting point, a middle point and an end point for at least a portion of the penetrating member.

14. An insertion device according to claim 1, wherein the insertion device comprises means to perform the following operations upon actuation of an activation part:
loading of a spring;
movement of the moving part from a start position to a stop position; and
transformation of said movement of the moving part to an insertion movement of the penetrating member, followed by a retraction movement of a holding means of the penetrating member.

15. An insertion device according to claim 14, further comprising a release member adapted to release the housing from a base part upon insertion of the penetrating member.

16. An insertion device according to claim 1, where the first direction form an angle $\beta$ to the surface in which the penetrating member is to be inserted, and where $30°<\beta<90°$.

17. An insertion device according to claim 1, wherein an energy storing member provides the energy required for moving the moving part from a start position to a stop position.

18. An insertion device according to claim 1, wherein the distance from the surface in which the penetrating member is inserted, is obtained by constructing the insertion device comprising an inclining proximal surface.

* * * * *